(12) United States Patent
Martin et al.

(10) Patent No.: US 8,793,618 B2
(45) Date of Patent: *Jul. 29, 2014

(54) LAUNCHING OF MULTIPLE DASHBOARD SETS THAT EACH CORRESPOND TO DIFFERENT STAGES OF A MULTI-STAGE MEDICAL PROCESS

(75) Inventors: Neil A. Martin, Encino, CA (US); Farzad D. Buxey, Marina Del Rey, CA (US)

(73) Assignee: The Regents of the University of California, Oakland, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 12/512,721

(22) Filed: Jul. 30, 2009

(65) Prior Publication Data

US 2010/0064374 A1    Mar. 11, 2010

Related U.S. Application Data

(60) Provisional application No. 61/137,518, filed on Jul. 30, 2008.

(51) Int. Cl.
  *G06F 3/048* (2013.01)
(52) U.S. Cl.
  USPC ........... 715/835; 715/774; 715/778; 715/779; 715/785; 715/846
(58) Field of Classification Search
  CPC ............ G06F 19/3406; G06F 19/3481; G06F 19/3418
  USPC .................. 715/785, 846, 774, 778, 779, 835
  See application file for complete search history.

(56) References Cited

U.S. PATENT DOCUMENTS

| 6,674,449 | B1 * | 1/2004 | Banks et al. ................... 715/740 |
| 7,058,901 | B1 * | 6/2006 | Hafey et al. ................... 715/792 |
| 2006/0265651 | A1 * | 11/2006 | Buck .............................. 715/700 |
| 2007/0067852 | A1 * | 3/2007 | James ............................. 726/28 |
| 2007/0101297 | A1 | 5/2007 | Forstall et al. |

(Continued)

FOREIGN PATENT DOCUMENTS

| EP | 1630666 A2 | 3/2006 |
| EP | 1865458 A1 | 12/2007 |

(Continued)

OTHER PUBLICATIONS

Hansen et al., "Moving Out of the Lab: Deploying Pervasive Technologies in a Hospital", Jul.-Sep. 2006, IEEE CS and IEEE ComSoc, Pervasive Computing IEEE vol. 5 Issue 3, pp. 25-26.*

(Continued)

*Primary Examiner* — Kieu Vu
*Assistant Examiner* — Aaron Lowenberger
(74) *Attorney, Agent, or Firm* — St. Onge Steward Johnston & Reens LLC

(57) ABSTRACT

A robust window pane display system and method for coordinating window pane displays in the form of dashboards to assist nurses and doctors in the treatment of a medical patient based upon various medical situations. The window pane display system may be linked to a computer or computer network. The system may involve multiple dashboards for a multi-stage procedure or operation having discrete dashboards for each stage of the multi-stage procedure. A method for creating new dashboards for use in the window pane display system.

29 Claims, 39 Drawing Sheets

(56) References Cited

U.S. PATENT DOCUMENTS

| | | |
|---|---|---|
| 2007/0130541 A1 | 6/2007 | Louch et al. |
| 2007/0185739 A1* | 8/2007 | Ober et al. .................. 705/3 |
| 2007/0255588 A1 | 11/2007 | Hamilton |
| 2007/0294281 A1* | 12/2007 | Ward et al. .................. 707/102 |
| 2008/0034314 A1 | 2/2008 | Louch et al. |
| 2008/0065422 A1 | 3/2008 | Weber |
| 2008/0126945 A1* | 5/2008 | Munkvold et al. ............ 715/733 |

FOREIGN PATENT DOCUMENTS

| | | |
|---|---|---|
| JP | 2001034690 A | 2/2001 |
| JP | 2003162586 A | 6/2003 |
| JP | 2007249818 A | 9/2007 |
| JP | 2007325742 A | 12/2007 |

OTHER PUBLICATIONS

European Search Report; Application No. EP 09 16 6889; Issued: Mar. 21, 2012; Mailing Date: Mar. 30, 2012; 7 pages.

European Search Report, Application No. EP 09 16 6889, Completed: Jan. 25, 2013; Mailing Date: Feb. 5, 2013, 15 pages.

* cited by examiner

LAUNCHING OF MULTIPLE DASHBOARD SETS THAT EACH CORRESPOND TO DIFFERENT STAGES OF A MULTI-STAGE MEDICAL PROCESS

CROSS-REFERENCE TO RELATED APPLICATIONS

The present application claims the benefit under 35 U.S.C. §119(e) of the Provisional Patent Application Ser. No. 61/137,518 entitled Launching of Multiple Dashboard Sets That Each Correspond to Different Stages of A Multi-Stage Medical Process", filed Jul. 30, 2008, and incorporates the contents of this provisional application herein by reference.

The present application is related to U.S. patent application Ser. No. 12/509,989, entitled "Single Select Clinical Informatics" filed on Jul. 27, 2009, and incorporates the contents of this application herein by reference.

FIELD OF THE INVENTION

This subject invention concerns the field of providing a robust window pane display system coordinating window pane displays to assist nurses and doctors in the treatment of a medical patient based upon various medical situations.

BACKGROUND OF THE INVENTION

In a hospital or medical facility, it is useful to use various technologies in order to assist in the doctors and nurses to view relevant patient information, for day-to-day use, and especially during a surgical operation. Nurses and doctors require access to the most relevant and up-to-date medical information for a patient and to have this information provided to them in an easy to read and easy to access format. This is important because providing doctors and nurses with relevant information assists and helps doctors and nurses in the treatment of patients. Additionally, nurses and doctors may require different information, as nurses typically require relevant information for day-to-day care of patients (e.g., blood pressure and heart rate), while doctors may require information relating to a patients long term care conditions, updates on medical conditions, and overall health (e.g., updates on cancerous growths, white blood cell count, etc.).

As such, it is desired to provide a robust method and system for displaying such relevant information for both doctors and nurses, and it is further desired for such a system to be dynamic. It is further desired for this dynamic system to display the most relevant information for a patient according to specifications of a specific user, such as a doctor or nurse. It is further desired for such a system to be able to be modified by users, whereby the display provided by the system and method can be modified based upon individual patients and based upon the specifications of the users.

SUMMARY OF THE INVENTION

Accordingly, it is an object of the present invention to provide a robust method for displaying relevant information for both doctors and nurses. It is a further object of the invention to provide a method and device which allows a user to switch between dashboards depending upon the information needed to be shown. It is another object of the invention allowing for an element to switch between dashboards, whereby a user can manually switch between dashboards, or such the element provides for automatic scrolling between dashboards. It is another object of the invention to provide for a method for creating a new dashboard, which can be saved, so that the system can be customized based upon the particular needs of a user, such as a doctor or nurse.

These and other objectives are achieved by providing a device for displaying clinical information comprising: an interface having a first display area and a second display area, and one or more dashboards, the one more dashboards each having one or more window panes, wherein a first dashboard is displayed in the first display area, and the remaining dashboards are displayed as selectable icons in the second display area, and wherein the first dashboard and the remaining dashboards can be switched by an element, wherein the element switches the first dashboard displayed in the first display area with a dashboard corresponding to a selectable icon displayed in the second display area.

The second display area may be either above the first display area, to the side of the first display area, or partially overlapping the first display area. The element that switches the first dashboard may be selected from a group consisting of a touch sensitive element, scrolling element, cursor, switch, automated element, tag, RFID tag, voice control, or wireless device.

In a preferred embodiment, the device has five dashboards for a five stage operation, whereby the five stages may be 1) a preference-card stage, 2) a time-out stage, 3) an anesthetic stage, 4) an operation stage, and 5) a post-operation stage.

The device may have each stage correspond to a dashboard, and the first display area and second display area may be monitors.

The device may allow for automatic scrolling of the dashboards and may be incorporated with a computer system, computer network, and/or input and output devices.

The invention further provides a method for launching clinical information comprising: providing an interface, providing one or more dashboards, displaying a first dashboard in a first display area of the interface, displaying the remaining dashboards as selectable icons in a second display area of the interface, selecting a selectable icon from the second display area, and displaying the dashboard corresponding to the selected selectable icon in the first display area, and displaying the first dashboard as a selectable icon in the second display area.

The method may further comprise selecting additional selectable icons to display additional dashboards in the first display area for a multi-stage procedure or operation, wherein the additional selectable icons selected are displayed in the first display area. The selecting step may further comprise an element that allows for a selectable icon from the second display area to be picked. This element may be selected from a group consisting of a touch sensitive element, scrolling element, cursor, switch, automated element, tag, RFID tag, voice control, or wireless device.

The element may allow for automated scrolling of the dashboards, or may allow for manual scrolling of the dashboards. The element may be worn or carried by a user, such as if the user is in close proximity to the system, the dashboards might switch based upon the configuration of the element, which may be based upon the preferences of the user.

The method may further allow for the first dashboard to be displayed as a selectable icon in the second display area. The method may allow for the first dashboard to have a predefined configuration based upon a selected user profile, and may allow for each of the dashboards to have multiple window panes.

The invention further comprises a method for launching clinical information comprising: providing an interface, and one or more dashboards, the one or more dashboards each having one or more window panes; displaying a first dashboard in a first display area of the interface; displaying the remaining dashboards as selectable icons in a second display area of the interface; selecting an item in a window pane of the first dashboard and displaying the corresponding dashboard configured to the item selected in the first display area of the interface. The window pane selected may correspond to a selectable icon and dashboard displayed in the second display area.

This method may further comprise hiding or closing the first dashboard in the first display area and displaying the corresponding dashboard configured to the item selected in the first display area. The corresponding dashboard configured to the item selected may be displayed in a third display area that partially overlaps the first display area. The dashboards may be linked form a multi-stage operation of multiple dashboards.

The invention further involves a method for creating a new dashboard comprising: displaying a dashboard with a first set of window panes; receiving a change request to create a new dashboard by changing the view of one or more window panes of the dashboard; changing the view of one or more window panes of the dashboard to display a second set of views; receiving a set of rules from a user for displaying the new dashboard; displaying the new dashboard; and saving the new dashboard to a database.

The method may further comprise linking the new dashboard to other dashboards, and/or keeping the need dashboard private. The method may involve determining if a user has permission to modify the dashboard.

A dashboard is defined as a collection of window panes that are part of a single display presentation. All the window panes of a dashboard can typically be collectively viewed in a display, although in some embodiments the dashboard (and hence some of its window panes) can extend beyond the boundaries of the display.

The information displayed in a window pane (also referred to as the "view" of a window pane) may be in different forms, including reports, lists, notes, graphs, images, etc. Each window pane can present one or more views of (1) one or more clinical data items (e.g., present a list or graph associated with a vital signal or lab measurement) or (2) established treatment guidelines or protocols (e.g., guidelines from public reference sources or from customized intramural institutional policies regarding particular conditions or measurements).

As mentioned above, the method of some embodiments starts (also referred to as "launches" or "instantiates") multiple dashboards for a multi-stage procedure or operation. In some embodiments, one of the launched dashboards is displayed at its full resolution in a first display area of the display device, while the other launched dashboards are displayed as selectable icons (e.g., displayed as selectable thumbnails) in a second display area of the display device (e.g., in a display area below, above or to the side of the first display area, or in a display area overlapping the bottom, the top, the left or the right side of the first display area). Some of these embodiments also display a selectable icon in the second display area for the dashboard that is being displayed in the first display area.

The selection of a selectable icon (e.g., a cursor click on the icon) in the second display area causes the display of the icon's associated dashboard in the first display area. In addition to this selection approach or in lieu of this approach, other embodiments use other techniques to display and navigate through the launched dashboards that are not being viewed at a particular time in the first display area. For instance, in the embodiments that display the dashboards on touch sensitive displays, some embodiments might allow a user to switch between the dashboards (i.e., to change the dashboard being displayed in the first display area) by swiping his or her hand over the display device in a particular direction (e.g., to the left or to the right). This swiping motion causes the first display area to switch from displaying a particular dashboard to one that is to the side of the particular dashboard that is opposite the direction of the swiping motion.

Some embodiments provide an automated technique for scrolling through the various dashboards associated with a multi-stage operation or procedure. For instance, some embodiments define five dashboards, or five sets of linked drill-down dashboards, for a five-stage operation. These five stages can be a preference-card stage (stage during which nurses gather instruments), a time-out stage (stage for verifying patient and operation), an anesthetic stage (stage for commencing the anesthetics), an operation stage, and a post-operation stage.

For such an operation, some embodiments launch five dashboards, one for each stage. Alternatively, they might launch five sets of drilled-down dashboards, one set for each stage. A set of drill-down dashboards are several dashboards that are linked together as described in U.S. patent application Ser. No. 12/036,281, entitled "Drill Down Clinical Information Dashboard," which is incorporated herein by reference.

An operating room typically includes one or more monitors that display the dashboards. Some such embodiments automate the scrolling through the dashboards on the operating room's monitors by (1) reading RFID tags that are associated with items (e.g., wristbands) worn by the practitioners and (2) displaying or suggesting the appropriate dashboard for display. For instance, some embodiments display on the monitors preference-card dashboard or dashboard set when they detect only nurse RFIDs in the operating room. When an anesthesiologist enters the room, these embodiments will detect his RFID and in response switch to the anesthetic stage dashboard or dashboard set, or provide a pop-up window asking whether such a dashboard or dashboard set should be displayed.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The novel features of the invention are set forth in the appended claims. However, for purpose of explanation, several embodiments are set forth in the following figures.

FIG. 2a illustrates a window displaying patient names and locations;

FIG. 2b illustrates a window displaying a lab report for "blood gasses" of a patient;

FIG. 5d illustrates a nursing information window displaying information relevant for nurses;

FIG. 5g illustrates a lab results window displaying several lab results;

DETAILED DESCRIPTION OF THE INVENTION

I. Overview

Figure 1:
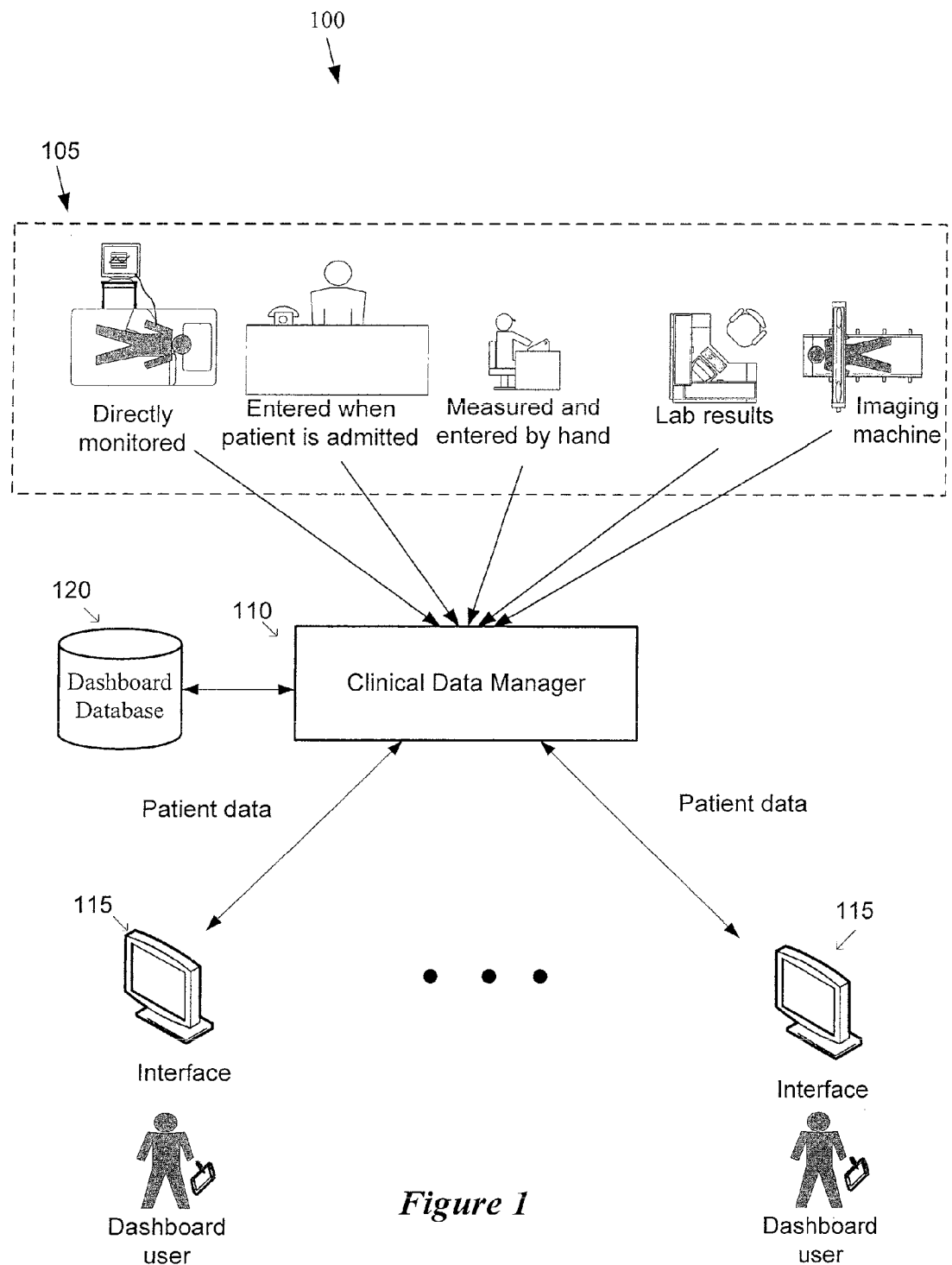
FIG. 1 illustrates a system architecture of some embodiments.

Some embodiments of the invention provide a robust method for launching clinical information regarding a multi-stage operation or operation in multiple dashboards. A dashboard is a collection of window panes that are part of a single display presentation. All the window panes of a dashboard can typically be collectively viewed in a display, although in some embodiments the dashboard (and hence some of its window panes) can extend beyond the boundaries of the display.

The information displayed in a window pane (also referred to as the "view" of a window pane) may be in different forms, including reports, lists, notes, graphs, images, etc. Each window pane can present one or more views of (1) one or more clinical data items (e.g., present a list or graph associated with a vital signal or lab measurement) or (2) established treatment guidelines or protocols (e.g., guidelines from public reference sources or from customized intramural institutional policies regarding particular conditions or measurements).

As mentioned above, the method of some embodiments starts (also referred to as "launches" or "instantiates") multiple dashboards for a multi-stage procedure or operation. In some embodiments, one of the launched dashboards is displayed at its full resolution in a first display area of the display device, while the other launched dashboards are displayed as selectable icons (e.g., displayed as selectable thumbnails) in a second display area of the display device (e.g., in a display area below, above or to the side of the first display area, or in a display area overlapping the bottom, the top, the left or the right side of the first display area). Some of these embodiments also display a selectable icon in the second display area for the dashboard that is being displayed in the first display area.

The selection of a selectable icon (e.g., a cursor click on the icon) in the second display area causes the display of the icon's associated dashboard in the first display area. In addition to this selection approach or in lieu of this approach, other embodiments use other techniques to display and navigate through the launched dashboards that are not being viewed at a particular time in the first display area. For instance, in the embodiments that display the dashboards on touch sensitive displays, some embodiments might allow a user to switch between the dashboards (i.e., to change the dashboard being displayed in the first display area) by swiping his or her hand over the display device in a particular direction (e.g., to the left or to the right). This swiping motion causes the first display area to switch from displaying a particular dashboard to one that is to the side of the particular dashboard that is opposite the direction of the swiping motion.

Some embodiments provide an automated technique for scrolling through the various dashboards associated with a multi-stage operation or procedure. For instance, some embodiments define five dashboards, or five sets of linked drill-down dashboards, for a five-stage operation. These five stages can be a preference-card stage (stage during which nurses gather instruments), a time-out stage (stage for verifying patient and operation), an anesthetic stage (stage for commencing the anesthetics), an operation stage and a post-operation stage.

For such an operation, some embodiments launch five dashboards, one for each stage. Alternatively, they might launch five sets of drilled-down dashboards, one set for each stage. A set of drill-down dashboards are several dashboards that are linked together as described in U.S. patent application Ser. No. 12/036,281, entitled "Drill Down Clinical Information Dashboard," which is incorporated herein by reference.

An operating room typically includes one or more monitors that display the dashboards. Some such embodiments automate the scrolling through the dashboards on the operating room's monitors by (1) reading RFID tags that are associated with items (e.g.) wristbands) worn by the practitioners and (2) displaying or suggesting the appropriate dashboard for display. For instance, some embodiments display on the monitors preference-card dashboard or dashboard set when they detect only nurse RFIDs in the operating room. When an anesthesiologist enters the room, these embodiments will detect his RFID and in response switch to the anesthetic stage dashboard or dashboard set, or provide a pop-up window asking whether such a dashboard or dashboard set should be displayed.

II. Drill Down Clinical Information Dashboard

A. Introduction

FIG. 1 illustrates the system architecture of some embodiments. Patient data is received from several disparate patient data sources 105 at clinical data manager 110. The clinical data manager 110 collects objective data such as vitals from monitors monitoring the patients, lab reports, and medical images (e.g., x-rays, Magnetic Resonance Imaging (MRI), Computed Tomography (CT) scans, etc.), and subjective data such as physicians' assessments, physicians' diagnosis, or physician treatment plans from the various data sources 105. This collection of data may come from one or more locations such as different labs and hospitals.

The clinical data manager 110 receives, normalizes, analyzes, and/or aggregates the patient data for the purposes of gathering data about individual patients (as a snapshot of a patient's data or as a record of the data over time), and/or for the purpose of comparing statistics among patients (in some cases including the change in statistics of each patient) for various reasons, for example, in order to efficiently allocate medical resources.

The clinical data manager 110 reports data, disseminates data, and/or alerts users to data through various clinical information interfaces 115. In some embodiments, these interfaces are different from each other depending on the job of the user within the medical system, or the particular terminal on which the interfaces are displayed, and/or the momentary needs of the individual user and/or patient. In some embodiments, the interfaces are different depending on the location. For example, a user in the cardiac intensive care unit will receive one set of data and a user in neurosurgery will receive a different set of data. As will be further described below, the interface may be different depending on a particular patient's diagnosis or condition. In some embodiments, the clinical data manager provides the data in real-time to the various interfaces 115.

Figure 2:
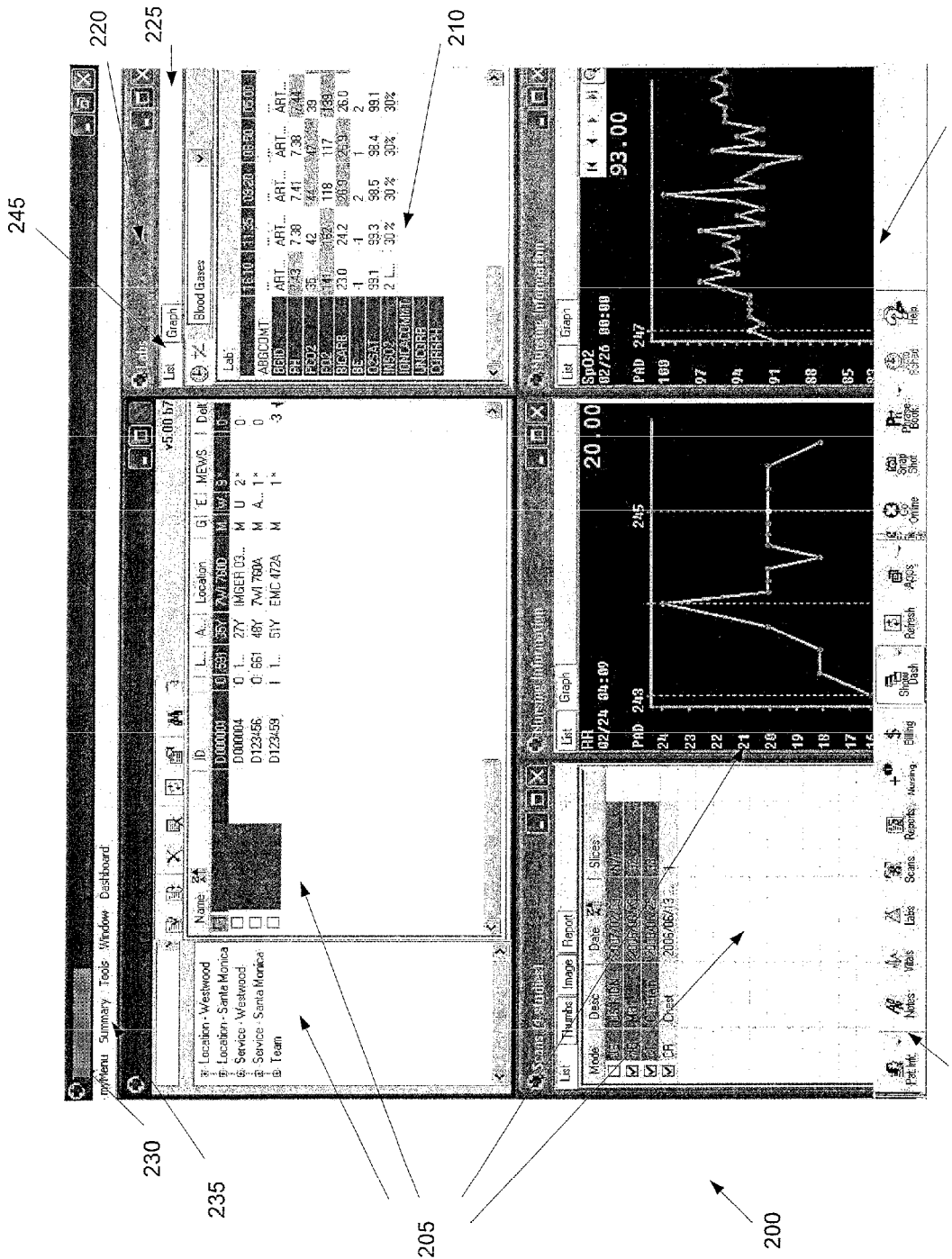
FIG. 2 illustrates an example of a dashboard of some embodiments.
Figure 2A:
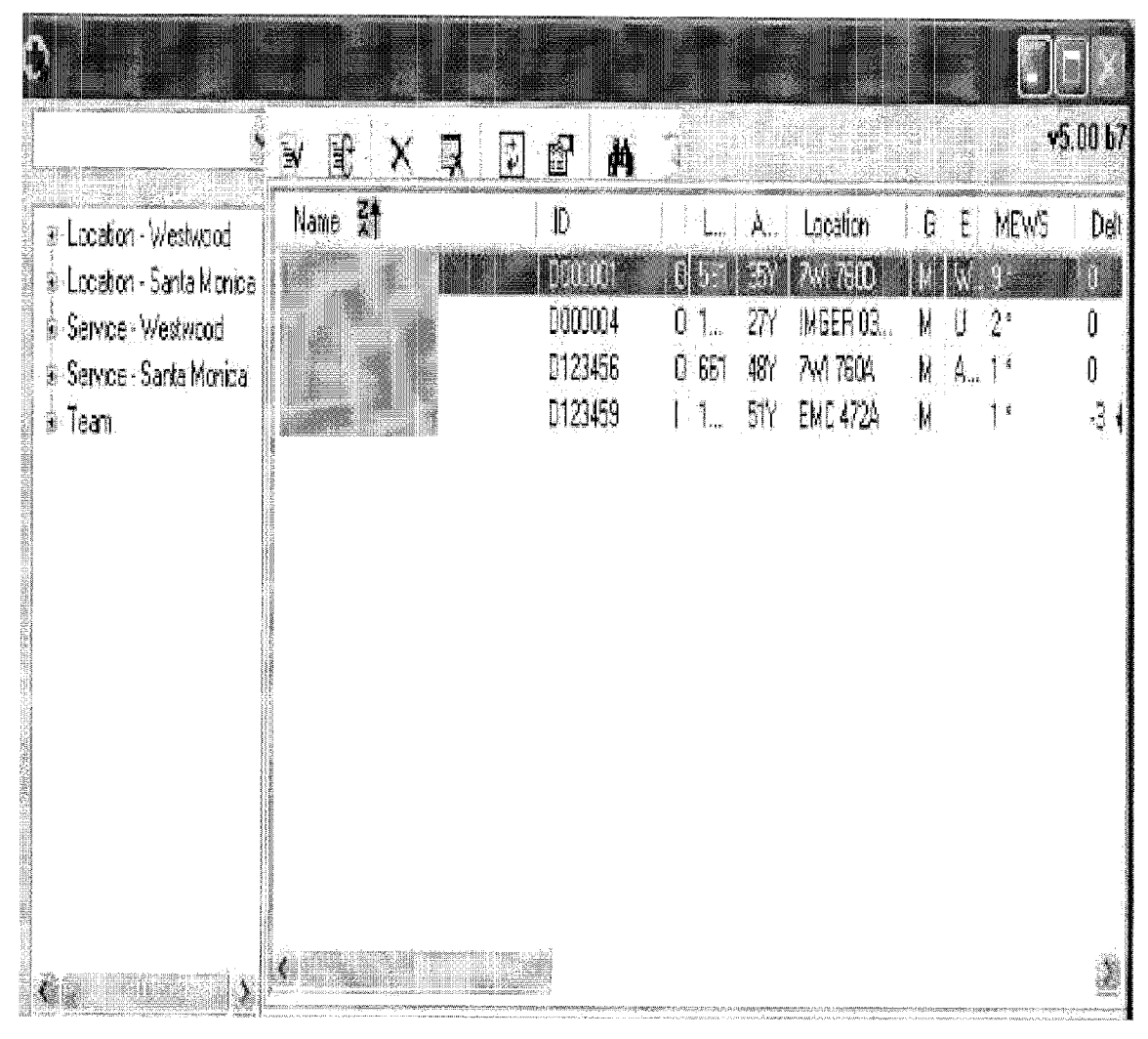
Figure 2B:
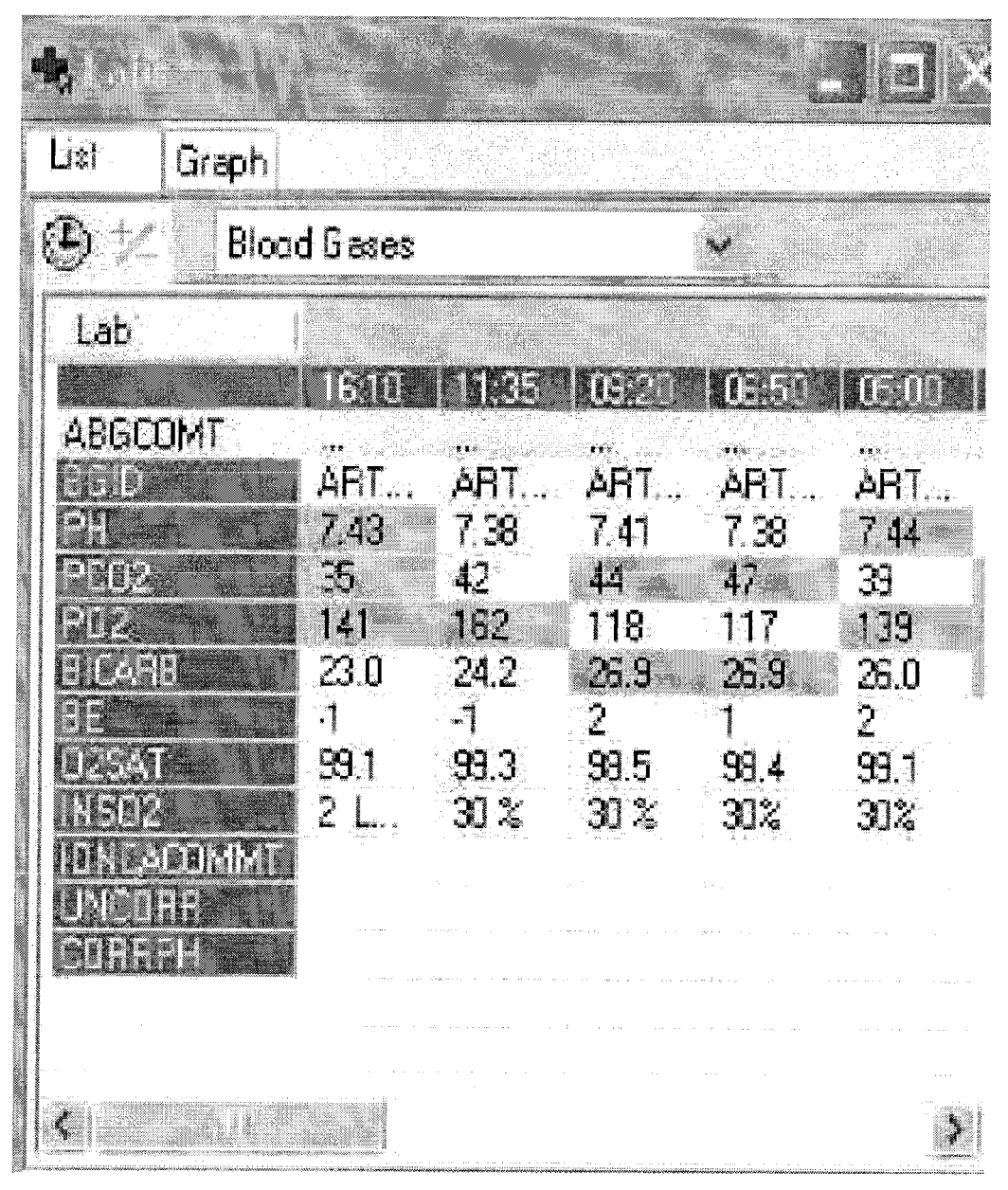
Figure 2C:
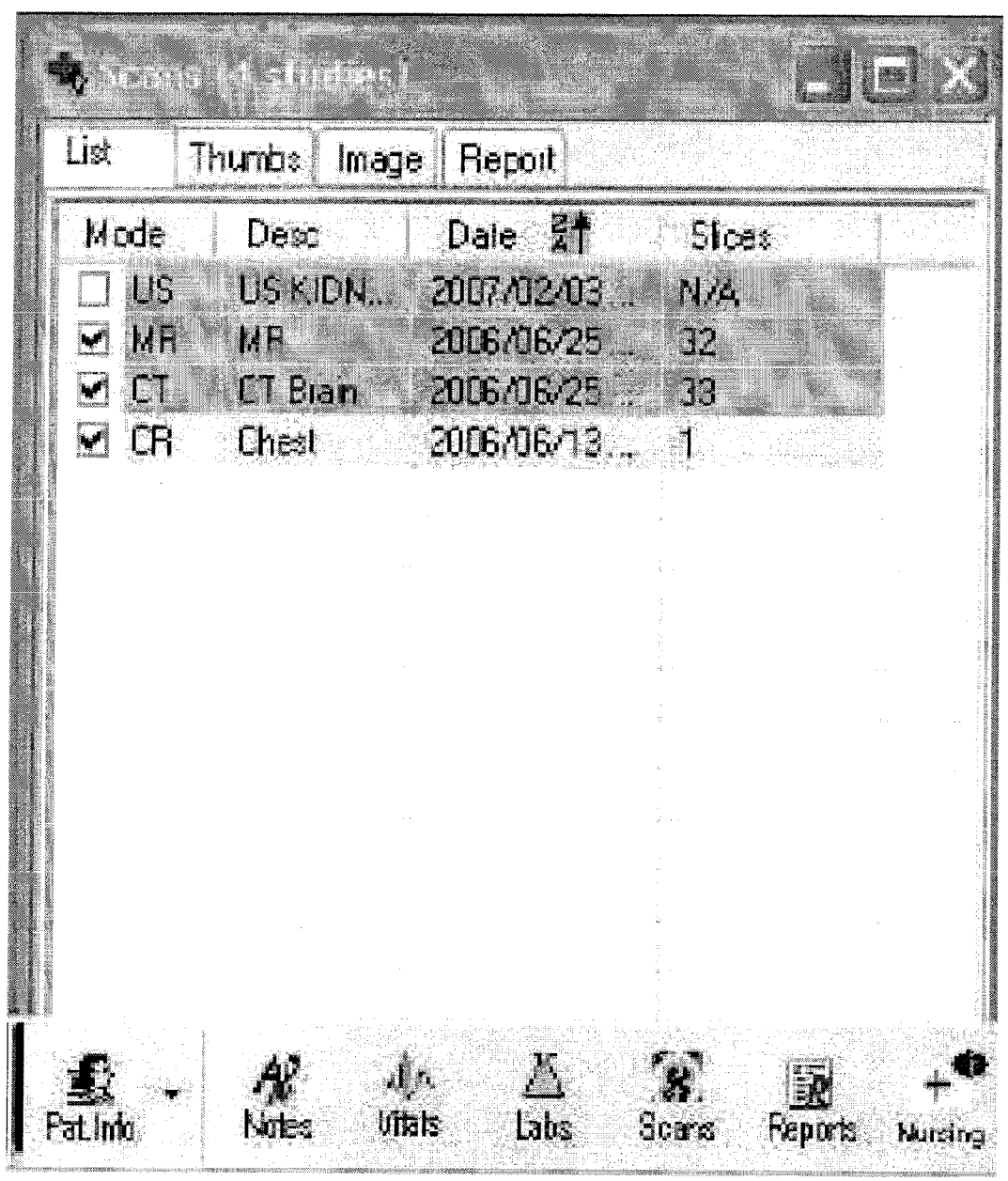
FIG. 2c illustrates a scan window displaying different modes and descriptions of various scans.
Figure 2D:
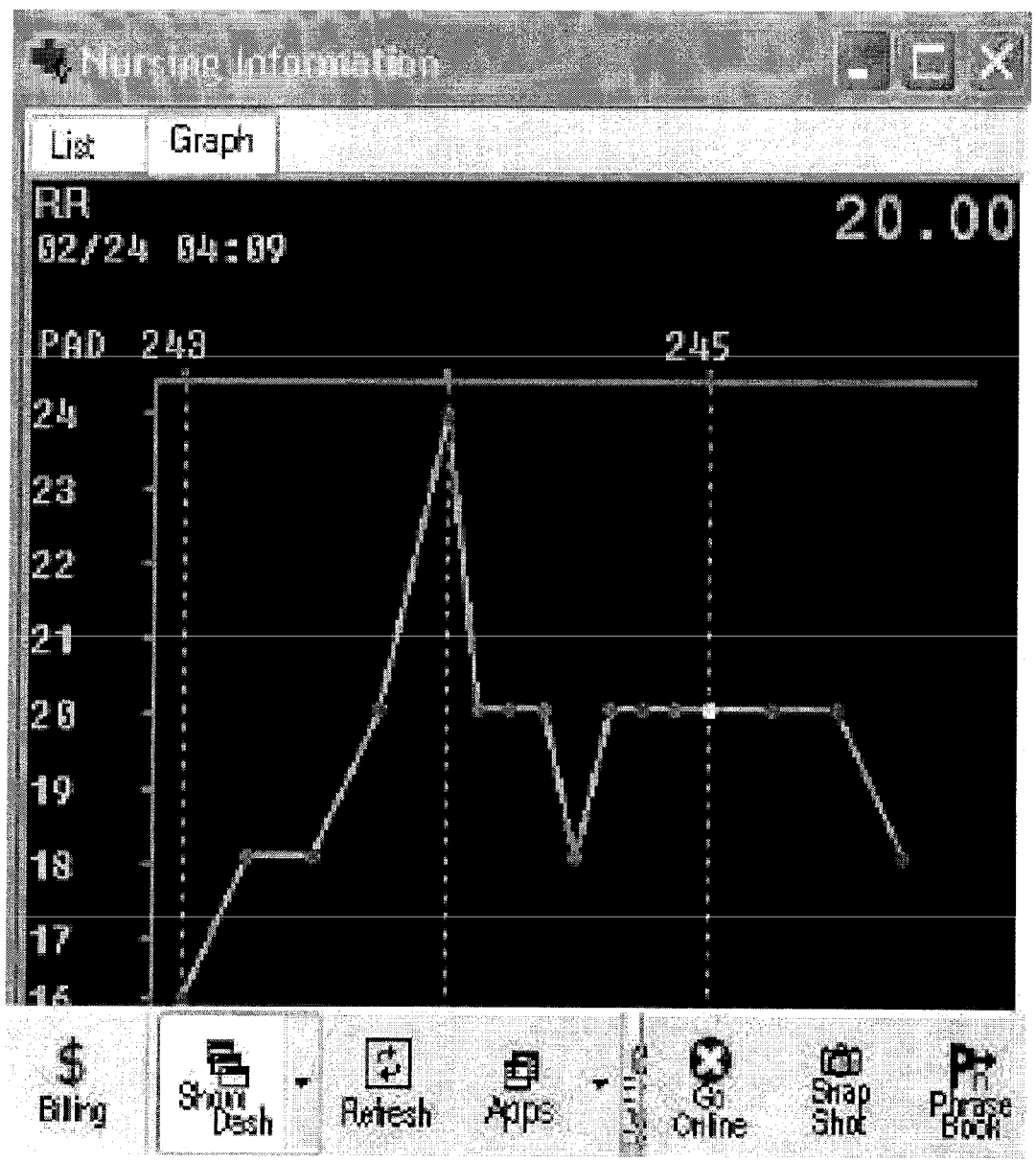
FIG. 2d illustrates a graph that depicts the percentage of (RR) of the patient over a period of time.

FIG. 2 provides an illustrative example of one such clinical information interface 200. As shown, the interface is provided graphically and includes (1) a title bar 230, (2) a menu bar 235, (3) a master toolbar 240, and (4) several windows 205. The master toolbar 240 appears at the bottom of the interface 200 and contains easy access to different application functionalities. For example, the master toolbar might include a button to refresh the clinical data, view lab results, view billing information, open up other windows, etc.

Several of the windows in the interface 200 display clinical data for one or more patients. The information displayed in a window pane (also referred to as the view of a window pane) may be in different forms, including reports, lists, notes, graphs, images, etc. For example, the information displayed may include the data needed to assess the severity of the patient's condition, the trend (e.g., improving and deteriorating) of the condition, the cause of the condition, the secondary consequences of the condition, etc. As illustrated, each window 205 can optionally have a title bar 220 that displays information about the window and a menu bar 225 that may include selectable tabs, pull-down menu, search bar, or various other tool buttons.

Figure 2E:
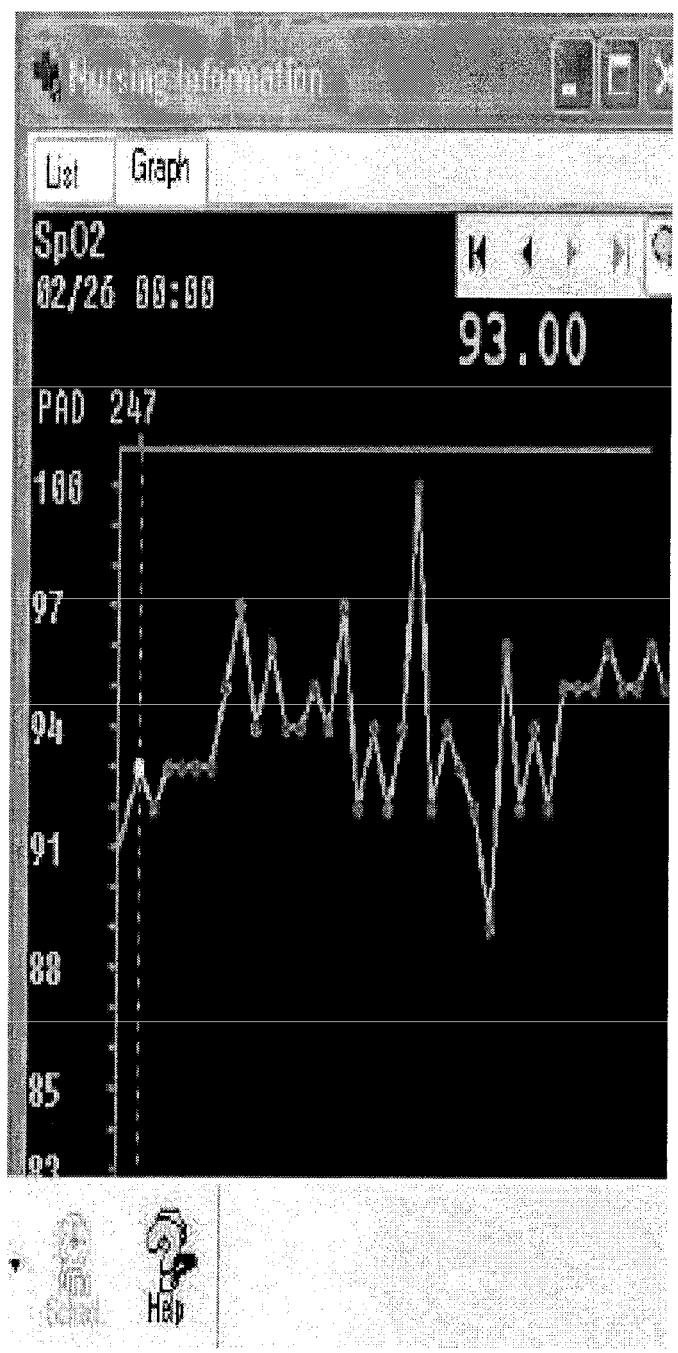
FIG. 2e illustrates a graph that depicts the percentage of oxygen saturation in blood (SpO2) of the patient over a period of time.

Several of the window panes present different views of one or more clinical data items. For instance window pane 210 (also shown in exploded format in FIG. 2b) provides a view for displaying a lab report for "blood gasses" of a patient. The lab report is presented as a list of measurement for several blood gases, and, in some cases, a particular item on the list can be expanded to present additional detail. However, the lab report can also be presented as a graph by selecting the item in the list and selecting a tab 245 in the menu bar 225. In some embodiments, the lab report can be presented as a graph by simply selecting the item (e.g., by double clicking the item) in the list. The view provided by the window pane 215 (also shown in exploded format in FIG. 2e) is an example of a graph that depicts the percentage of oxygen saturation in blood (SpO2) of the patient over a period of time. In some embodiments, the information that is displayed in the view may include established treatments, guidelines, or protocols. Such guidelines may come from public reference sources, or from customized intramural institutional policies. For instance, when a patient is diagnosed with hyperglycemia, one of the views of a dashboard may present a university's policy on how the condition is treated.

The collection of one of more window panes 205-210 is referred to as a dashboard. Some embodiments provide a robust methodology for presenting dashboards. This methodology allows two dashboards to be linked together such that while viewing a first dashboard, a second dashboard can be opened up upon selection of an item in the first dashboard. In some embodiments, when the second dashboard is opened, the first dashboard is automatically minimized, hidden or, in some cases, closed. In some embodiments, when the second dashboard is opened, the first dashboard is arranged in a manner so that both dashboards can be viewed concurrently.

In some embodiments, the linking of the dashboards is based on what the user most wants to see. Specifically, the information that is displayed in one or more views of the dashboard is designed and configured with intent to follow the typical train of thought and sequence of assessments of a trained or experienced professional such as a doctor. For example, one dashboard might link to a spreadsheet often most relevant lab results over time, or might lead to a trend plot of one or two key lab results over time. This allows the user of the interface to obtain the most relevant information without having to sort through the mass of information.

Some embodiments not only allow linking of dashboards but also allow the dashboard to be opened up to a predefined configuration. In this way, the user is initially presented with the most relevant information. This concept of initially presenting the most relevant information is also referred to as the drill down concept because it drills through the masses of data and quickly pulls out the data that the user wants to see first. For example, rather than starting with a view containing a list of all radiology scans of a patient, the dashboard may be configured to start with a view of a current chest x-ray and a view of a previous chest x-ray. Therefore, instead of pulling data out by a pull model (e.g., selecting different links to receive the relevant data), some embodiments of dashboard utilize a push model that pushes the relevant data out as a first view. In some embodiments, the different configurations of the dashboards are provided and stored in the dashboard library or database 120 as shown in FIG. 1. In some embodiments, the relevant data is not only pulled from medical facilities, but are pulled from different servers across the Internet (e.g., library, educational institutions, etc.).

Several more detailed embodiments of the invention are described in sections below. Specifically, Section III describes a multi-phase informatics display using several pre-configured dashboards during different phases of a medical operation. Finally, Section IV provides a description of a computer system with which some embodiments of the invention are implemented.

B. Linking of Different Dashboards

Some embodiments provide a hierarchy of dashboards where different dashboards can be linked to each other. In some embodiments, an initial set of these dashboards is pre-configured and are available for a user to view clinical information for one or more patients. A user can start from a top level dashboard and activate another dashboard by selecting an item or link in the current dashboard.

Figure 3:
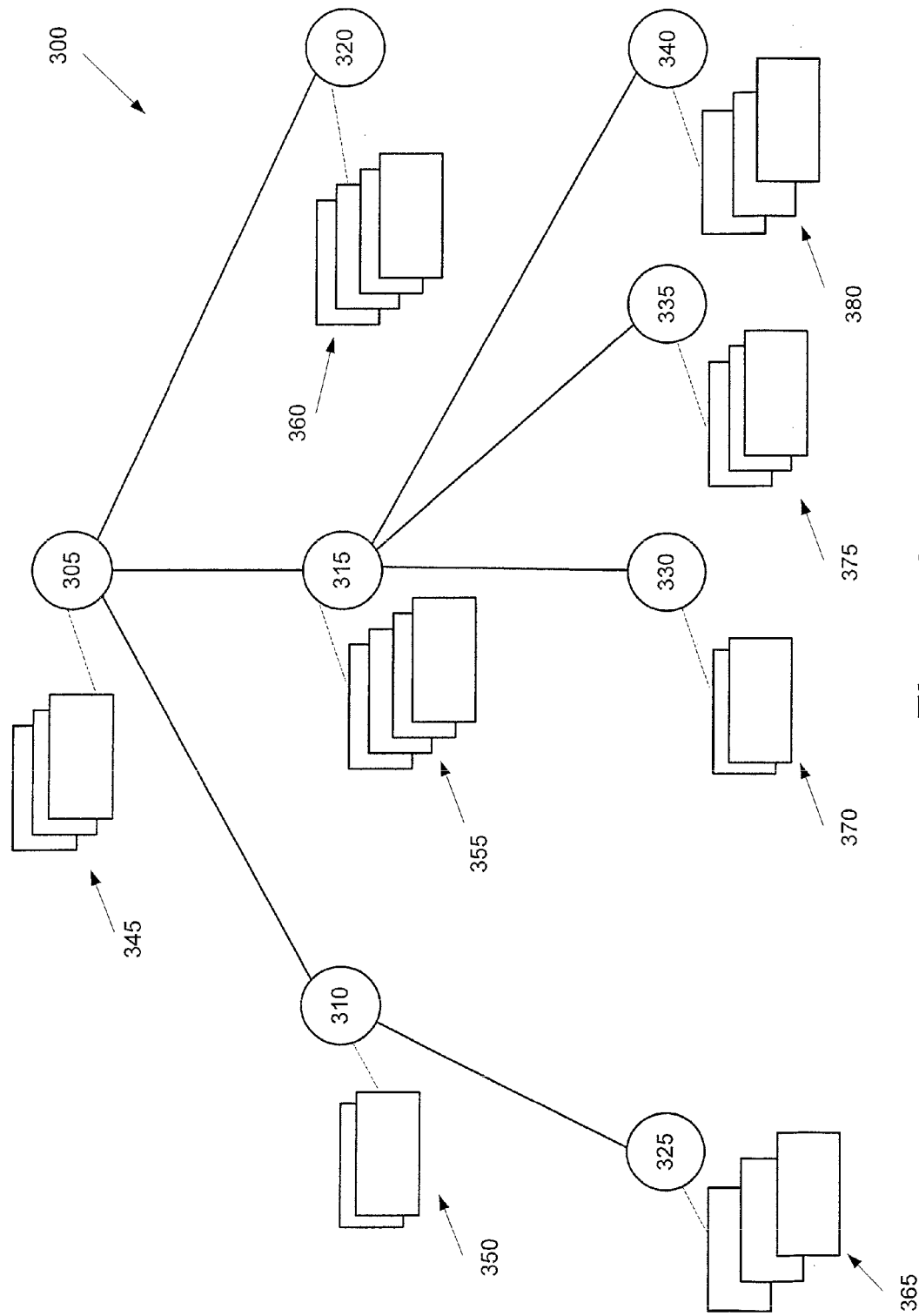
FIG. 3 illustrates a hierarchy of dashboards that provides an example of linking different dashboards together.

FIG. 3 illustrates a hierarchy 300 of dashboards in some embodiments. The figure includes a top level node 305 and several other nodes 310-340. Each node of the hierarchy represents one particular dashboard. Each dashboard has one or more window panes 345-380 associated with it. For instance, dashboard 325 has three windows panes 365. Each window pane provides a specific view for one or more clinical data items. For instance, these windows might show different information for a particular patient. One window pane might show a CT scan of the patient, the other window pane might show a lab report, and the third window might show a graph of oxygen saturation.

Also, as shown in FIG. 3, each dashboard might be linked to one or more other dashboards. For instance, dashboard 315 is linked to three other dashboards 330-340. Each one of these dashboards are activated when an item is selected (e.g., by double clicking on a displayed item in a window pane) in dashboard 315. In some embodiments, the activation or display of another dashboard minimizes, hides, or closes the currently selected dashboard.

In some embodiments, the linking of the dashboards is based on what the user most wants to see. As specified above, the information that is displayed in one or more views of the dashboard is designed and configured with intent to follow the typical train of thought and sequence of assessments of an experienced or trained professional. This allows the user of the interface to obtain the most relevant data without having to sort through the different collections of data.

Figure 4:
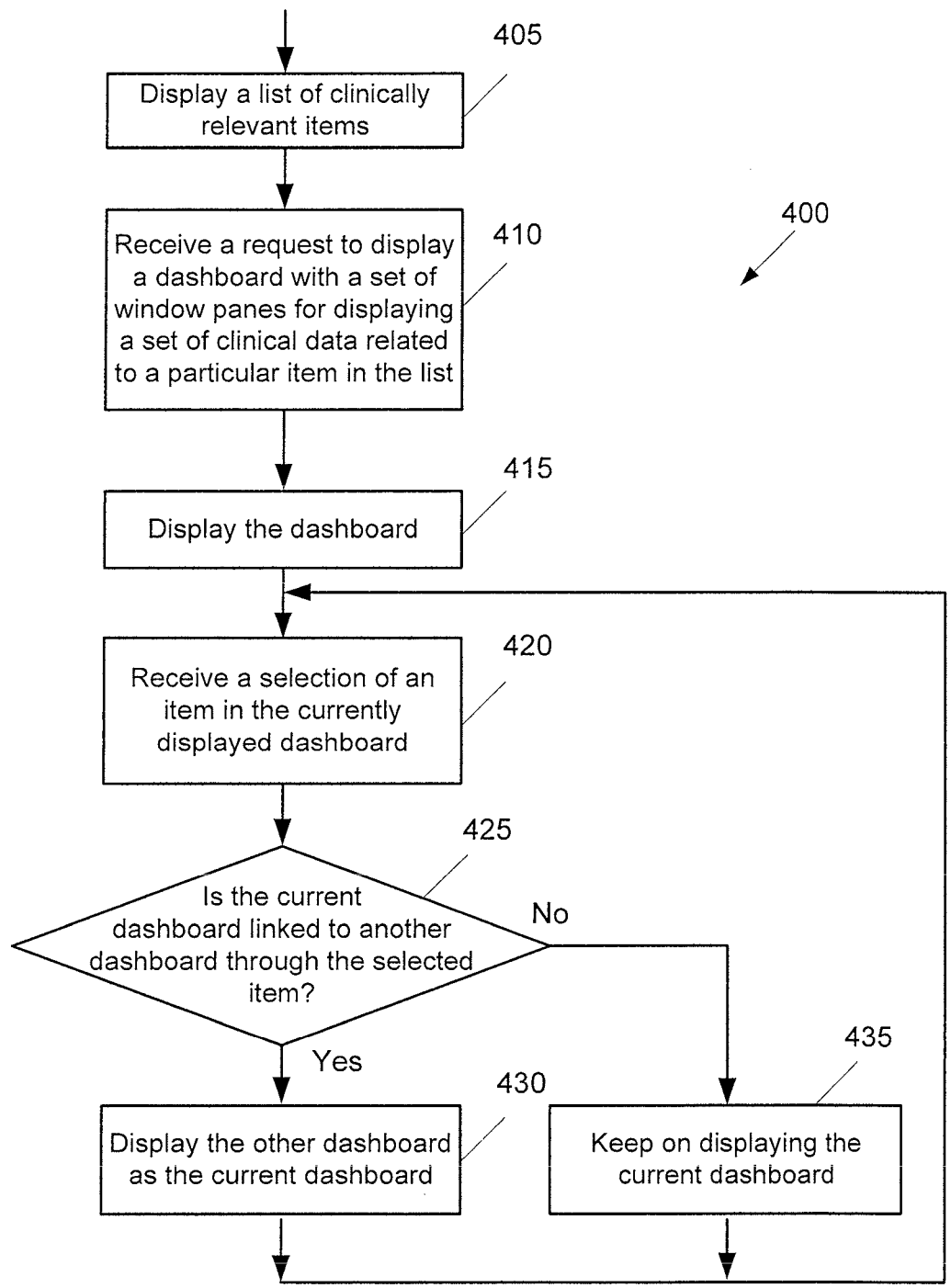
FIG. 4 conceptually illustrates a process for linking different dashboards together in some embodiments.

FIG. 4 conceptually illustrates a process 400 for linking different dashboards together in some embodiments. As shown, the process displays (at 405) a list of clinically relevant data in a clinical information interface. For instance, the process may display a list of different patients in a particular ward in a hospital, a list of all patients of a particular physician, or a list of all patients with a particular disease. In some cases, the process may display a summary window that contains information about one or more patients.

Figure 5:
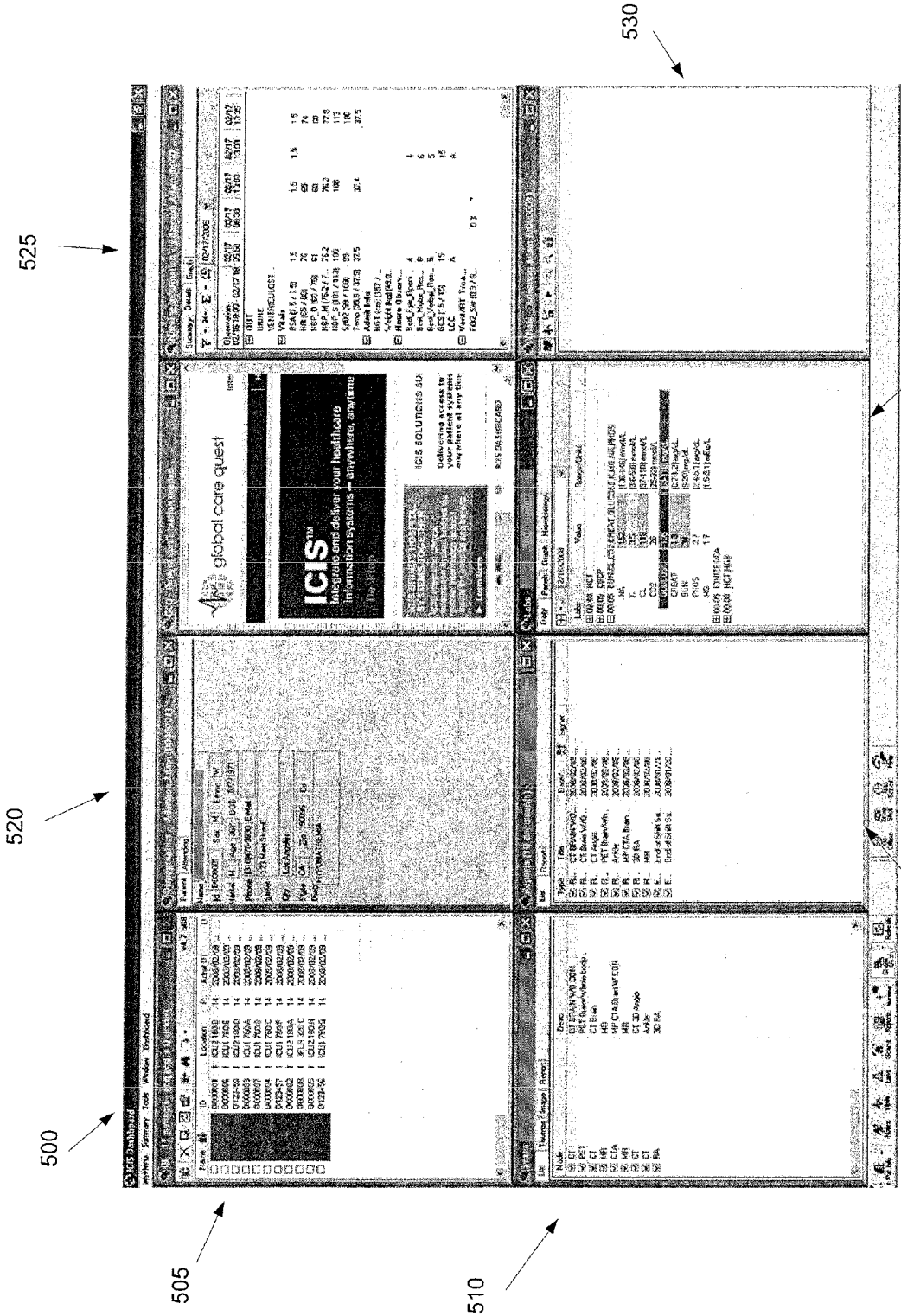
FIG. 5 illustrates example of a dashboard that links to another dashboard.
Figure 5A:
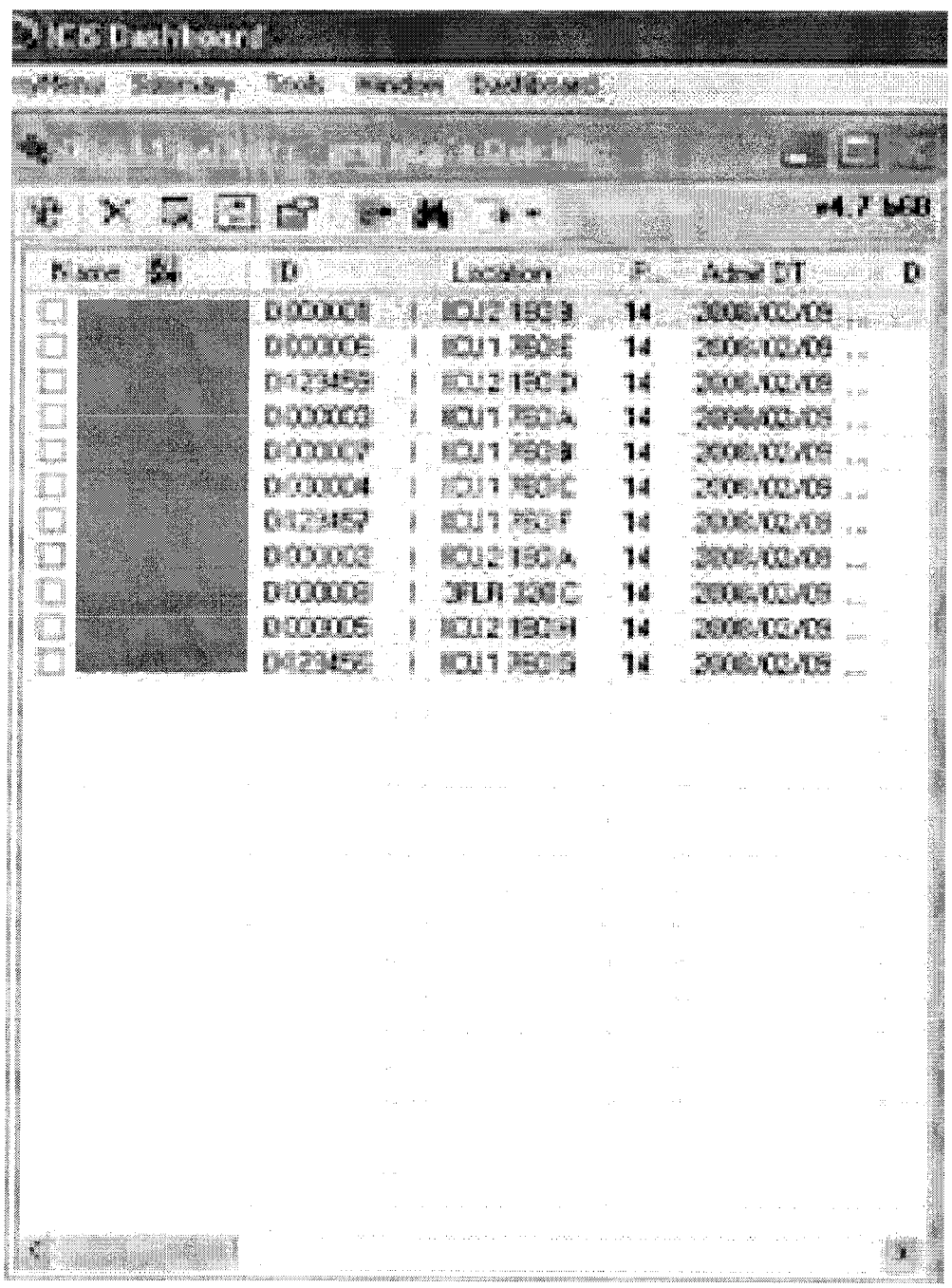
FIG. 5a illustrates a patient list window displaying patient names.

Next, at 410, the process receives a request for displaying a dashboard with a set of panes for displaying a set of clinical data related to a particular item in the list. For instance, a physician might click on the name of a patient to display data related to that patient. The process then displays (at 415) the dashboard. FIG. 5 provides one such example of a dashboard 500 that is displayed when a patient is selected from a patient list window 505 (also shown in FIG. 5a). Specifically, this dashboard displays several window panes that include clinical data for a patient selected from the patient list window 505. In some embodiments, the patient list window 505 is not considered part of the dashboard.

Figure 5B:
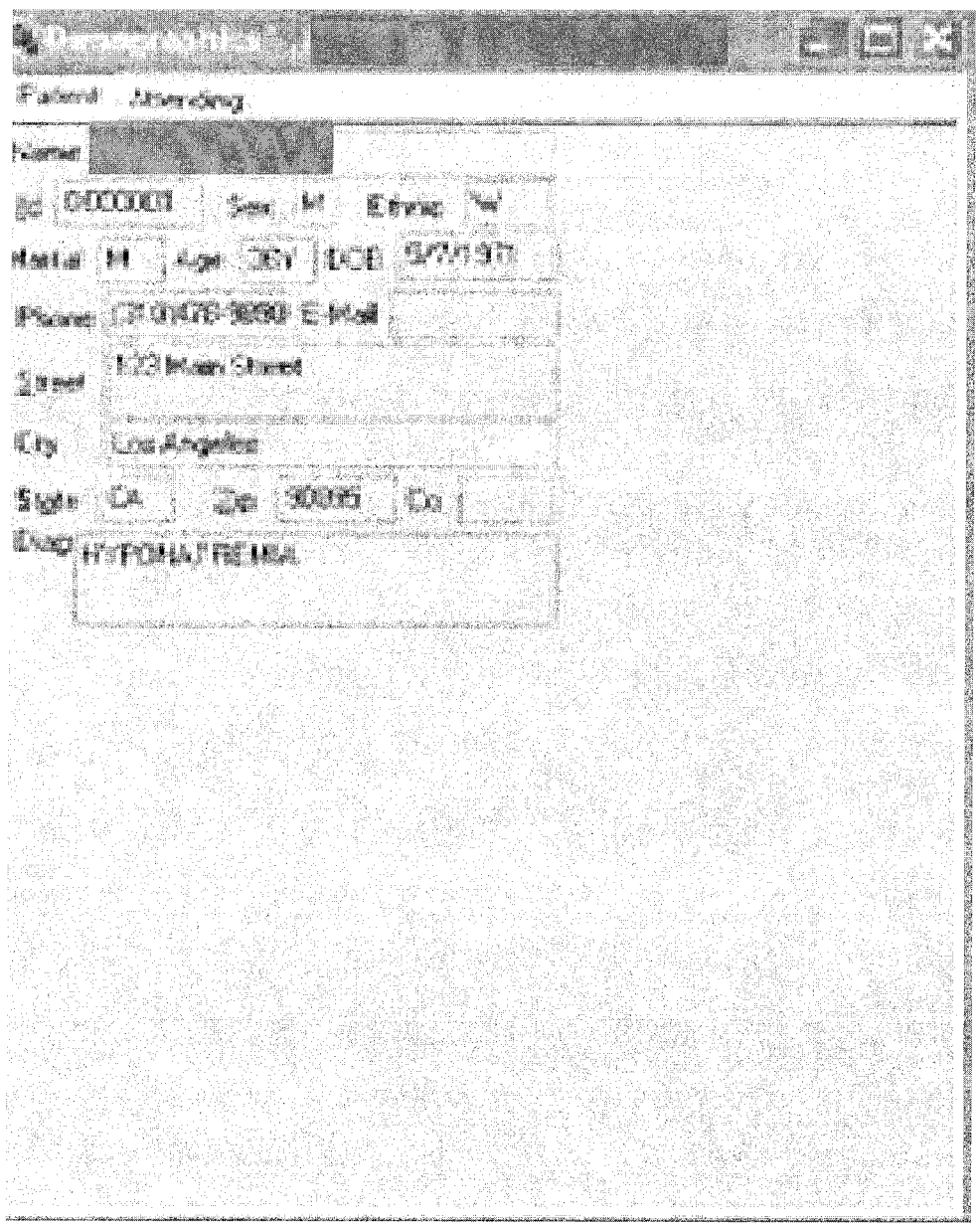
FIG. 5b illustrates a demographics window displaying a patient's demographic.
Figure 5C:
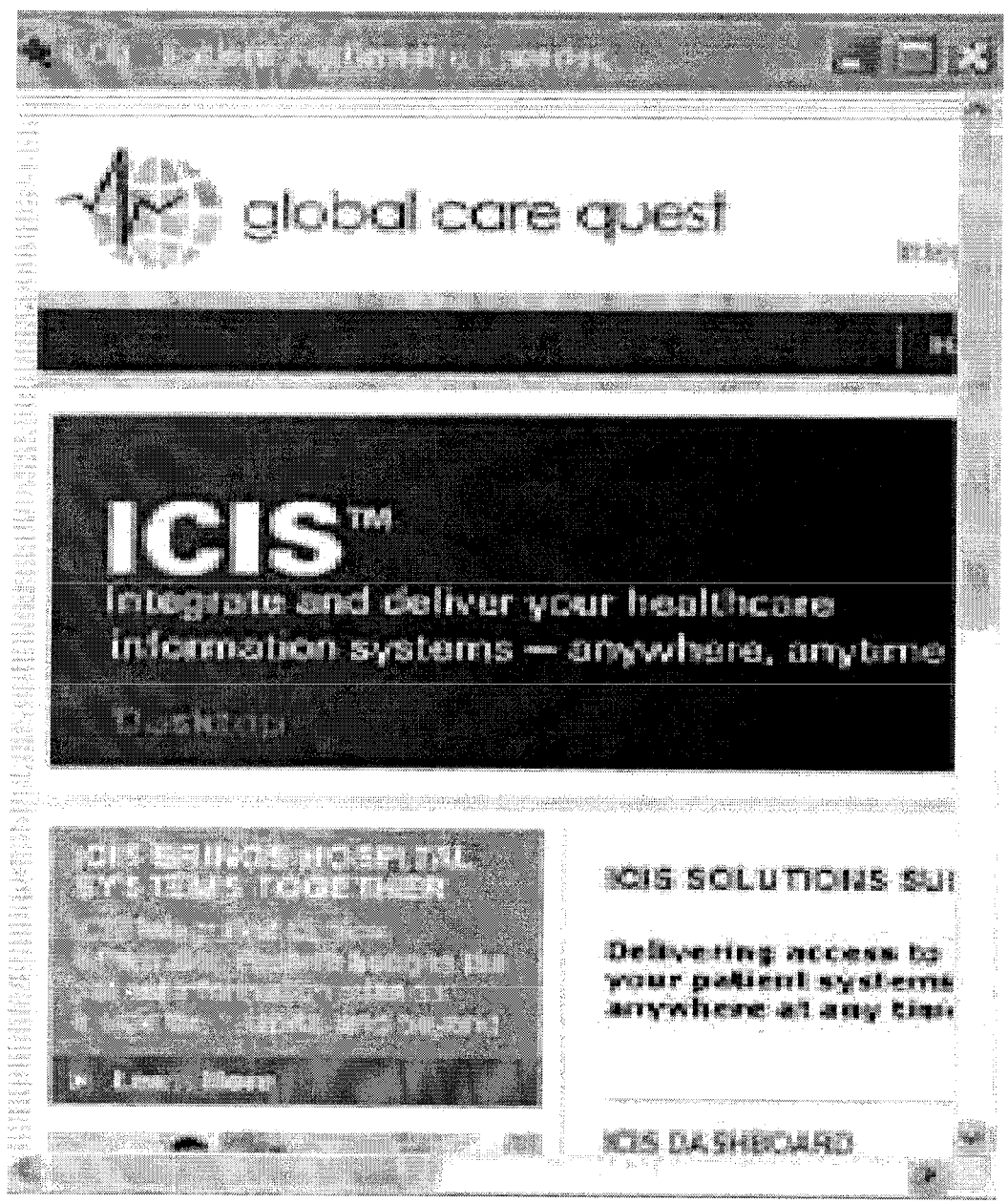
FIG. 5c illustrates a window displaying the global care quest information.
Figure 5D:
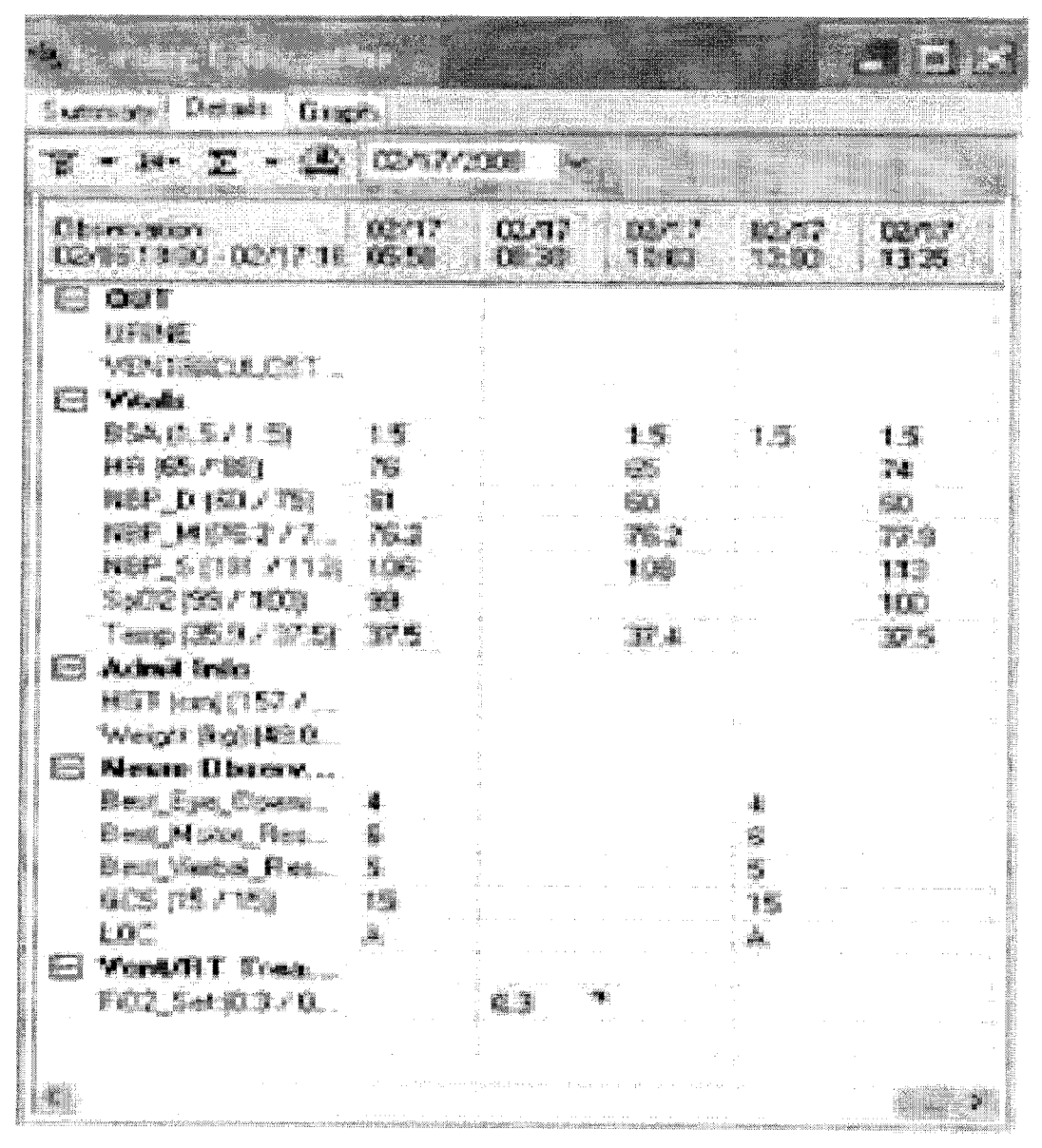
Figure 5E:
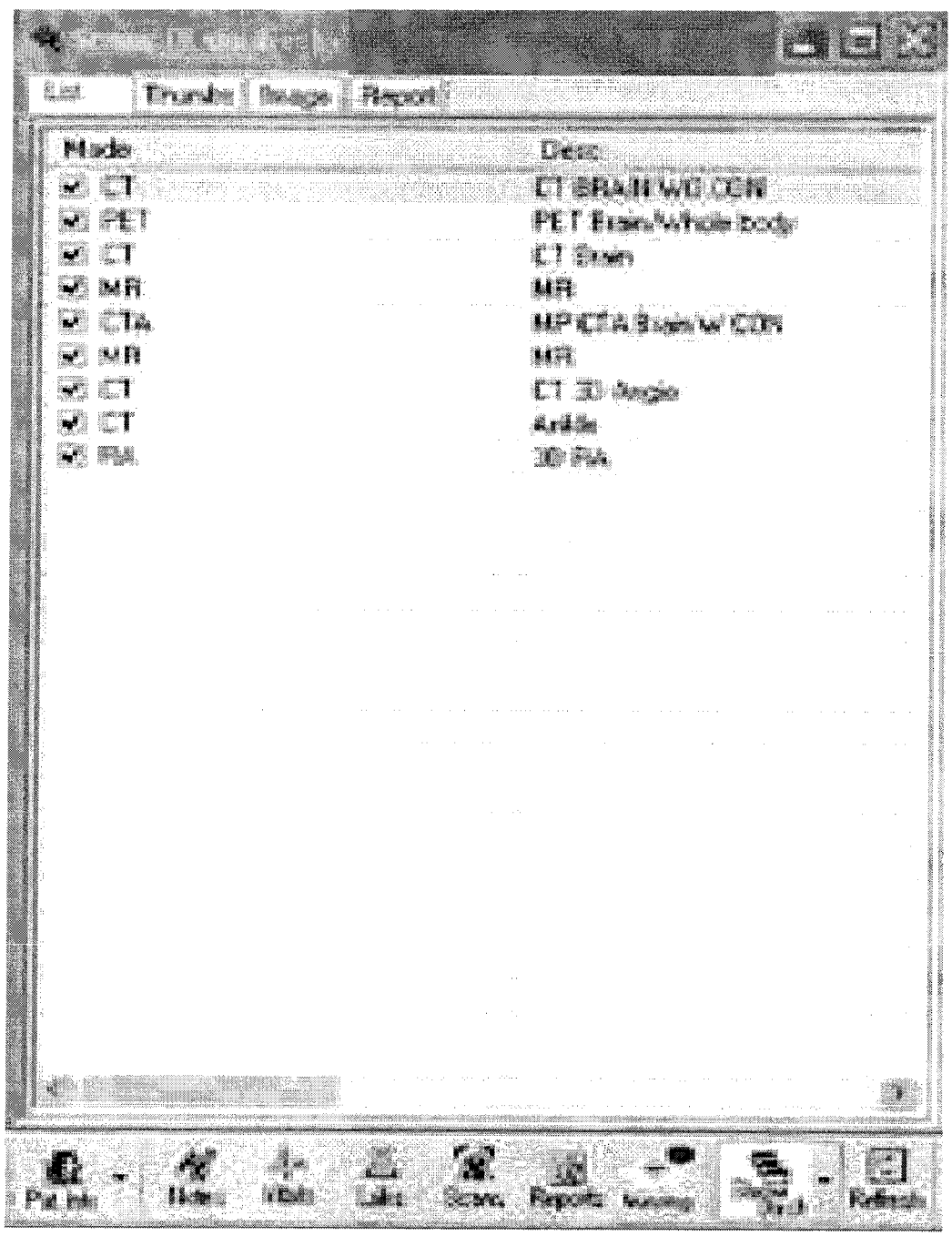
FIG. 5e illustrates a scan result window displaying a patient's scan results.
Figure 5F:
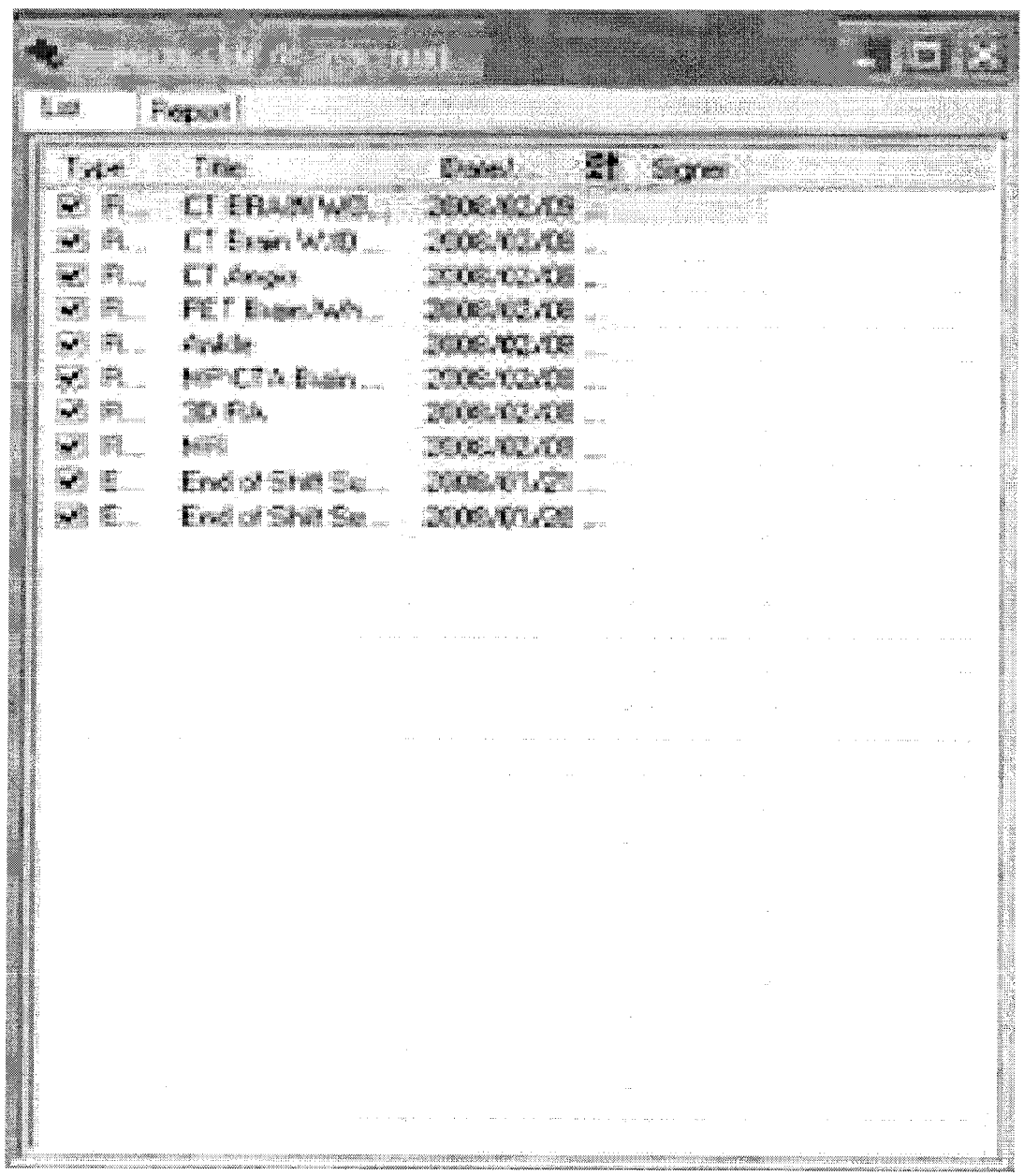
FIG. 5f illustrates a reports window displaying the patient's reports.
Figure 5G:
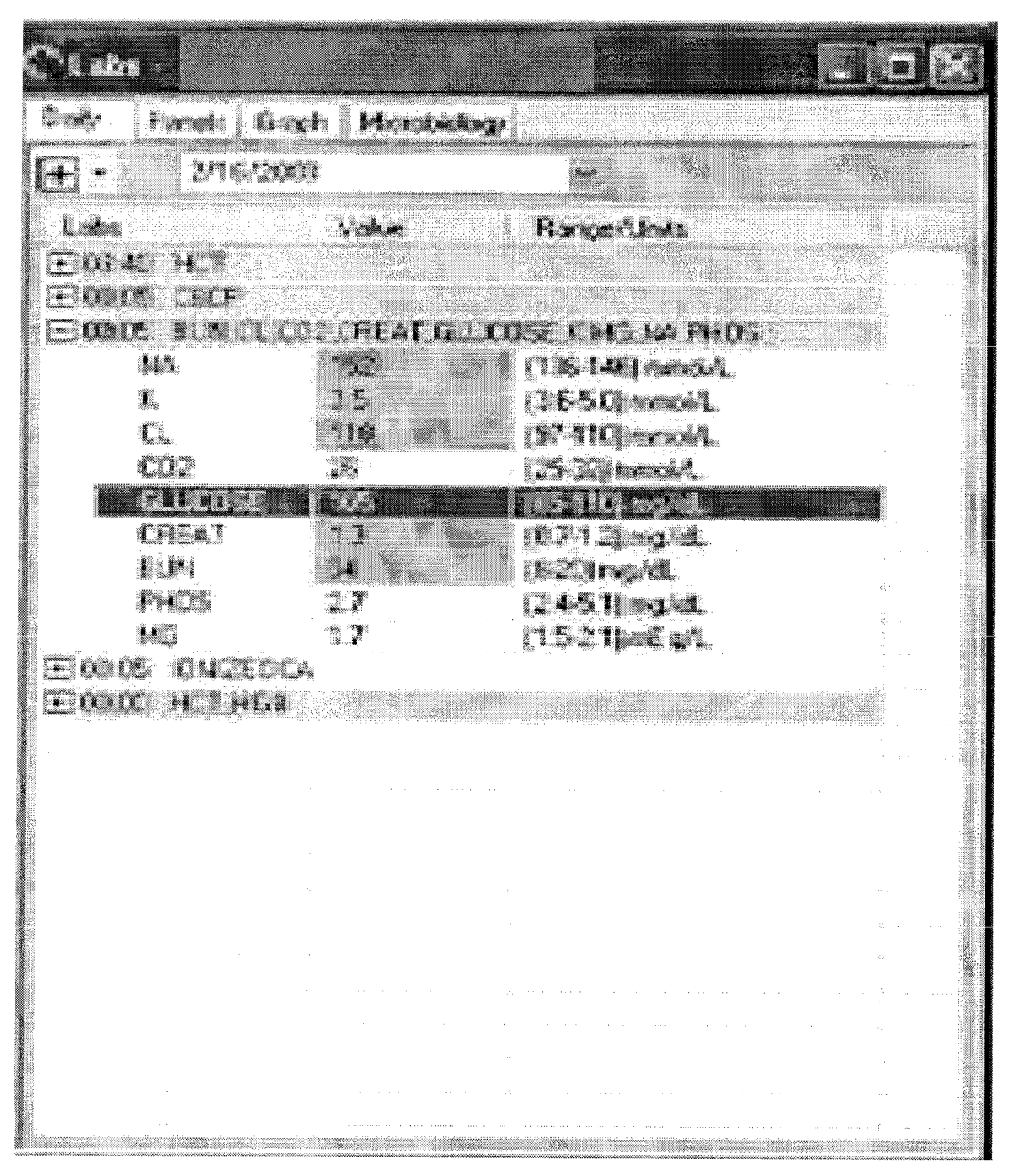
Figure 5H:
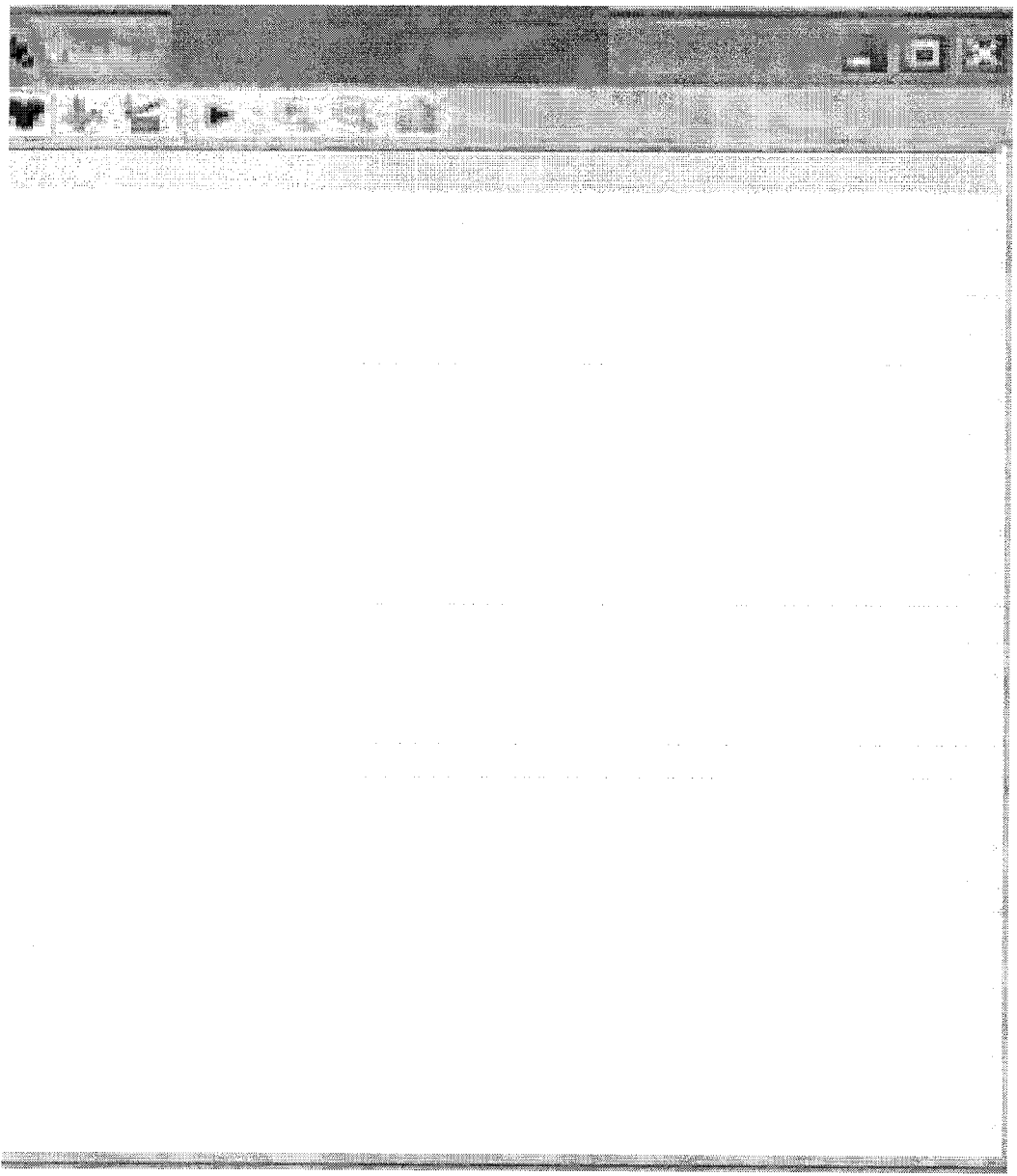
FIG. 5h illustrates a vitals window displaying the patient's vitals.

As illustrated in FIG. 5, when a user selects a patient from the patient list window, the user is presented with dashboard 500 that includes (1) a scan result window 510 (also shown in exploded format in FIG. 5e) that displays a patient's scan results, (2) lab results 515 window (also shown in exploded format in FIG. 5g) that displays several lab results, (3) demographics window 520 (also shown in exploded format in FIG. 5b) that displays the patient's demographic, (4) nursing information window 525 (also shown in exploded format in FIG. 5d) that displays nursing information, (5) vitals window 530 (also shown in exploded format in FIG. 5h) that displays the patient's vitals, and (6) reports windows 535 (also shown in exploded format in FIG. 5f) that displays the patient's reports.

Next, at 420, the process receives an indication that an item is selected in the dashboard. Referring back to FIG. 3, a dashboard (such as 315) might be linked to several other dashboards 330-340 through different items in the dashboard. When one of those items is selected (e.g., with click on that item), the corresponding dashboard is displayed. For instance, a view of a window may include a link to several recommended dashboards for a particular condition. In some embodiments, when a particular item is selected (e.g., when a user right-clicks or otherwise selects in some manner), the user is presented with one or more recommended dashboards. In some embodiments, selecting an item causes an existing view of window pane that shows recommended dashboards to show recommend dashboards related to that selected item. In this way, the user is able to navigate from one dashboard to another dashboard in order to easily view relevant data.

Figure 6:
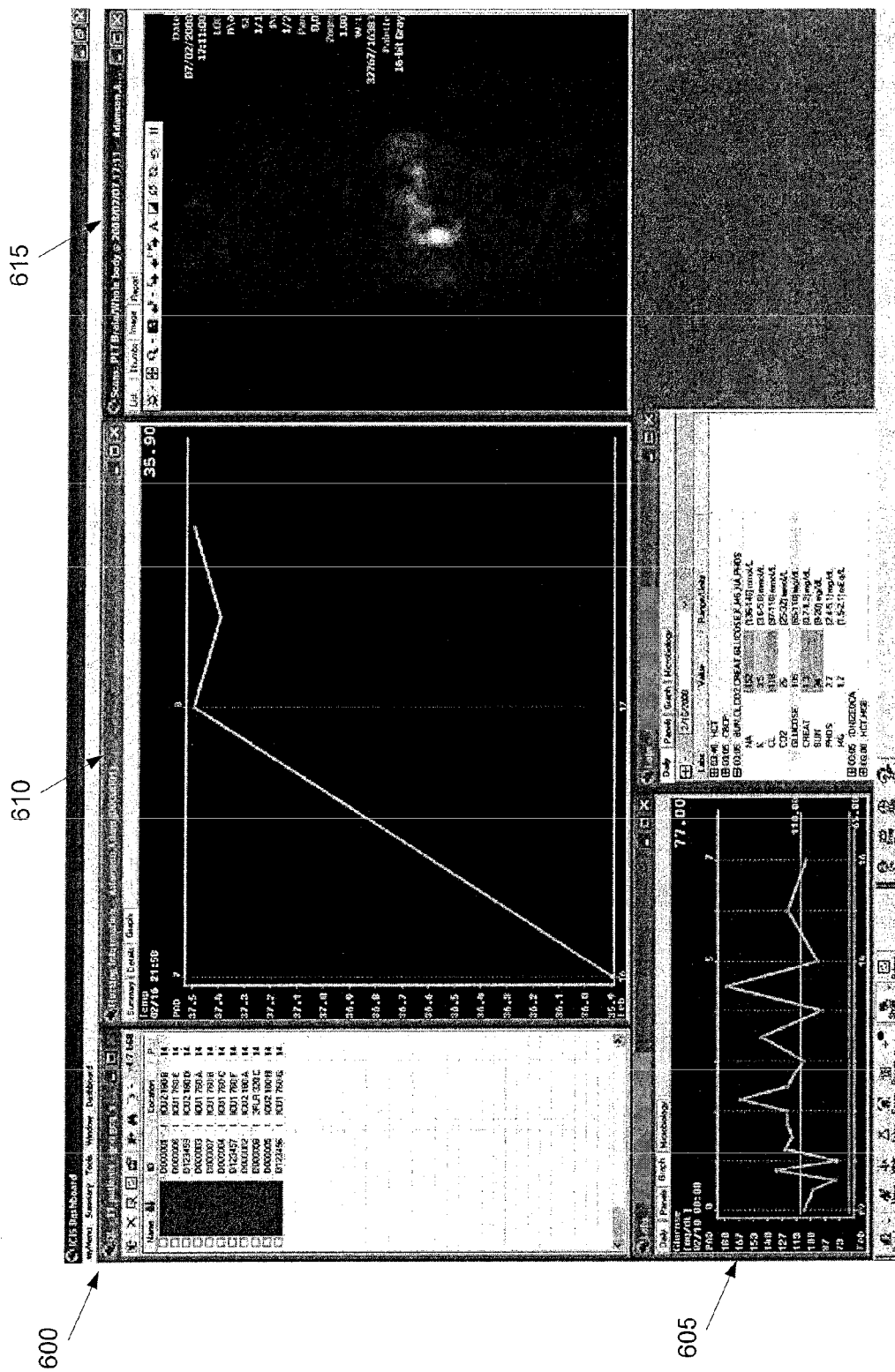
FIG. 6 illustrates an example of a dashboard that is linked to the dashboard as illustrated in FIG. 5.
Figure 6A:
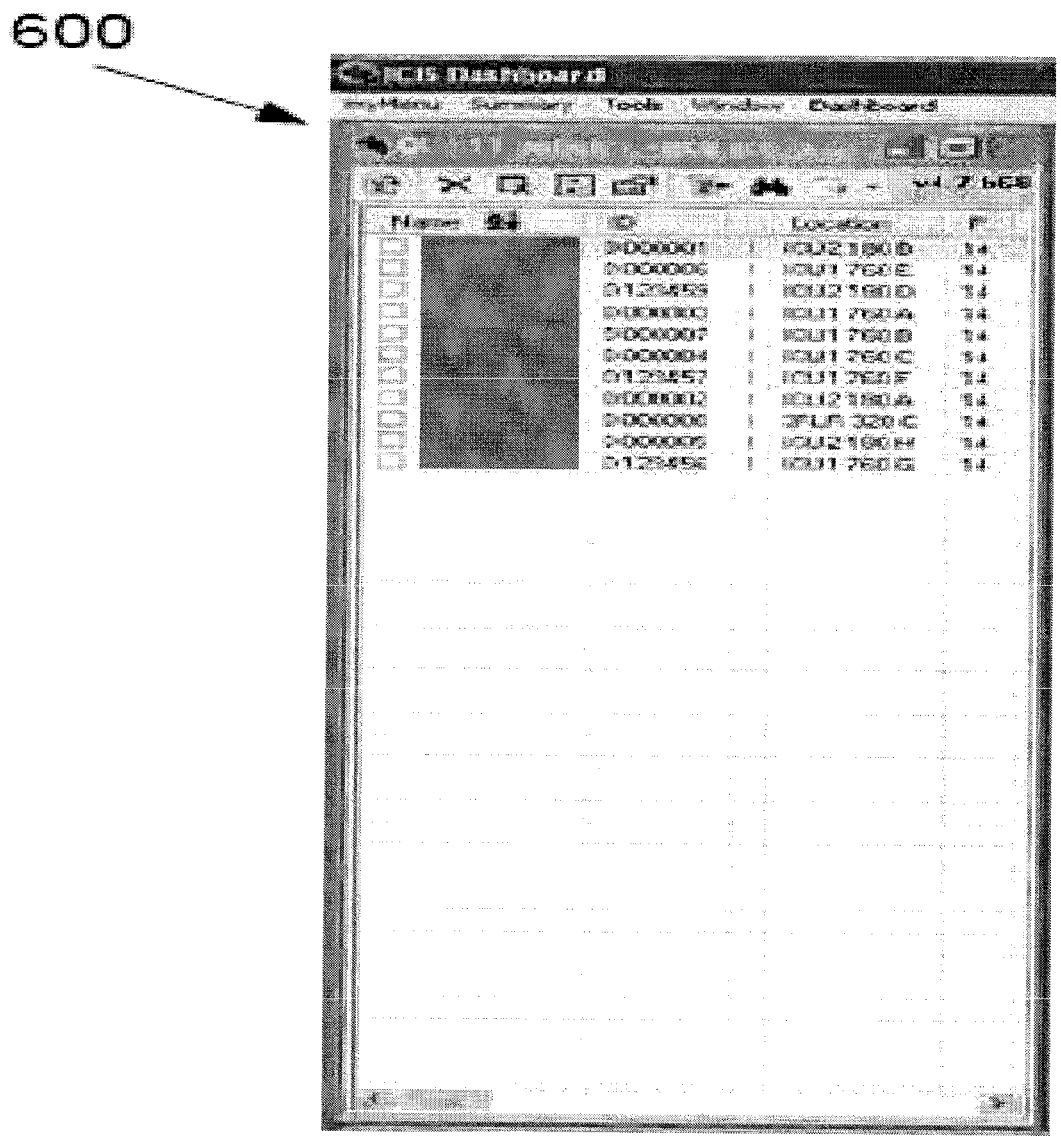
FIG. 6a illustrates a patient list window displaying patient names.
Figure 6B:
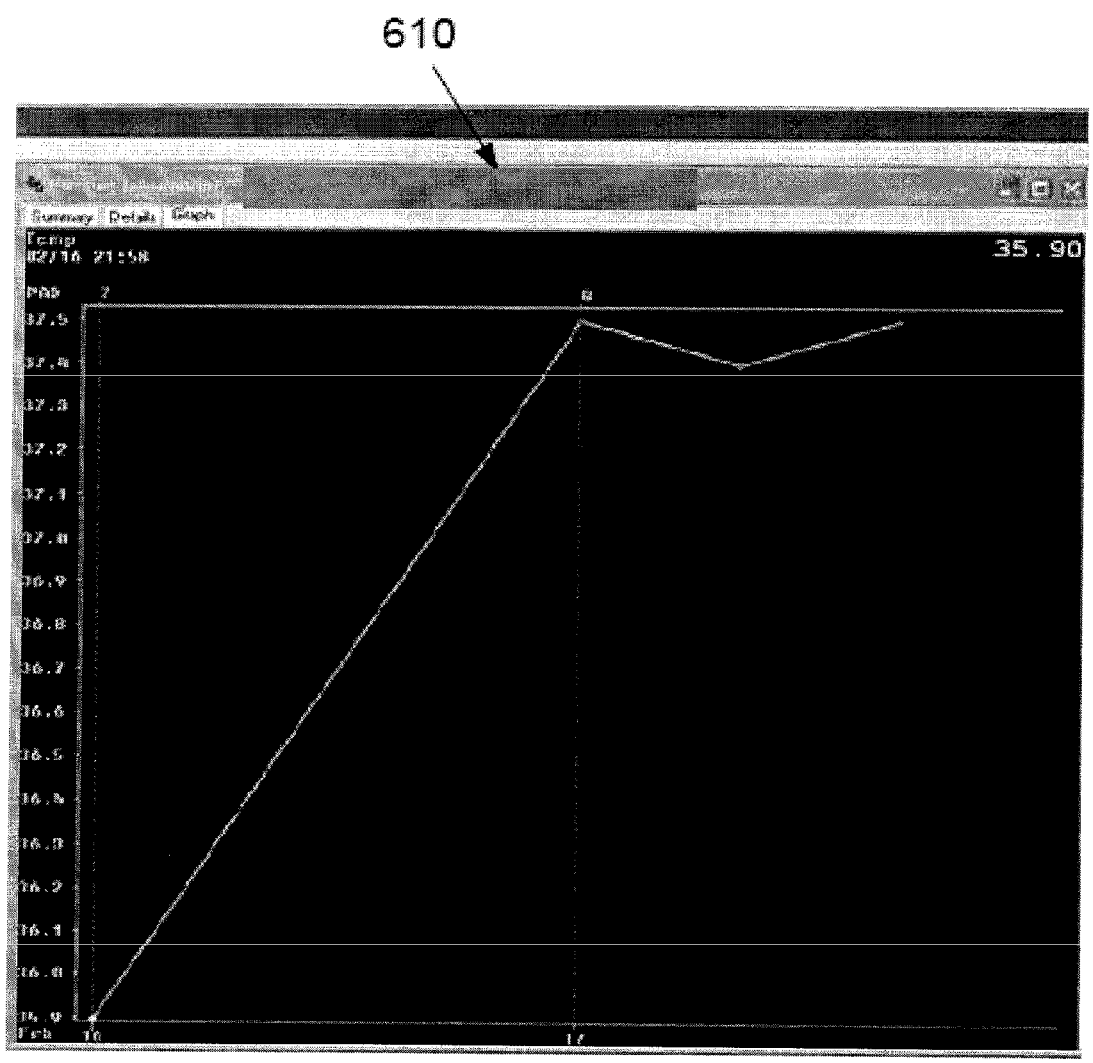
FIG. 6b illustrates a graph of temperature values over time.
Figure 6C:
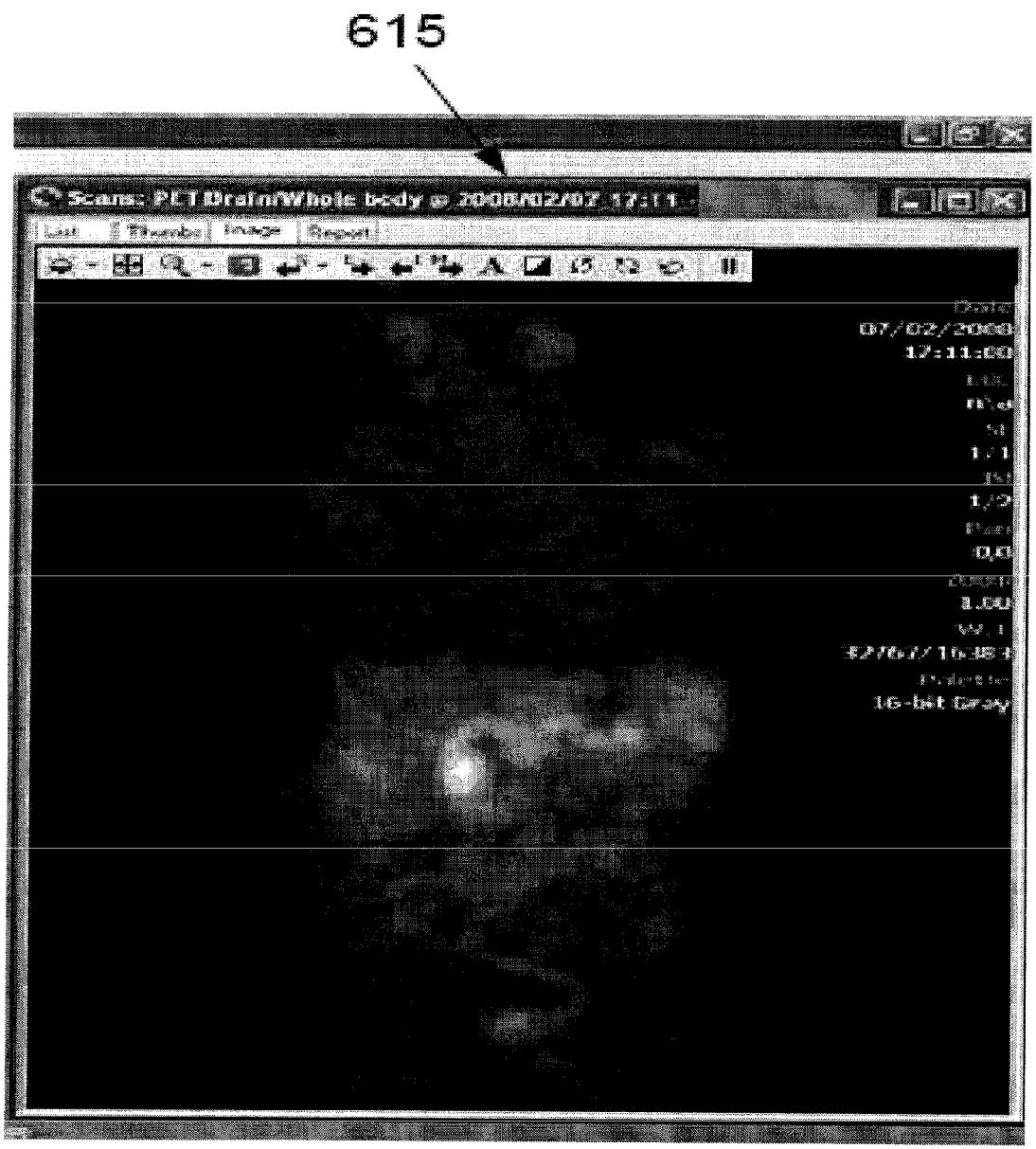
FIG. 6c illustrates a window displaying a x-ray of the body of a patient.
Figure 6D:
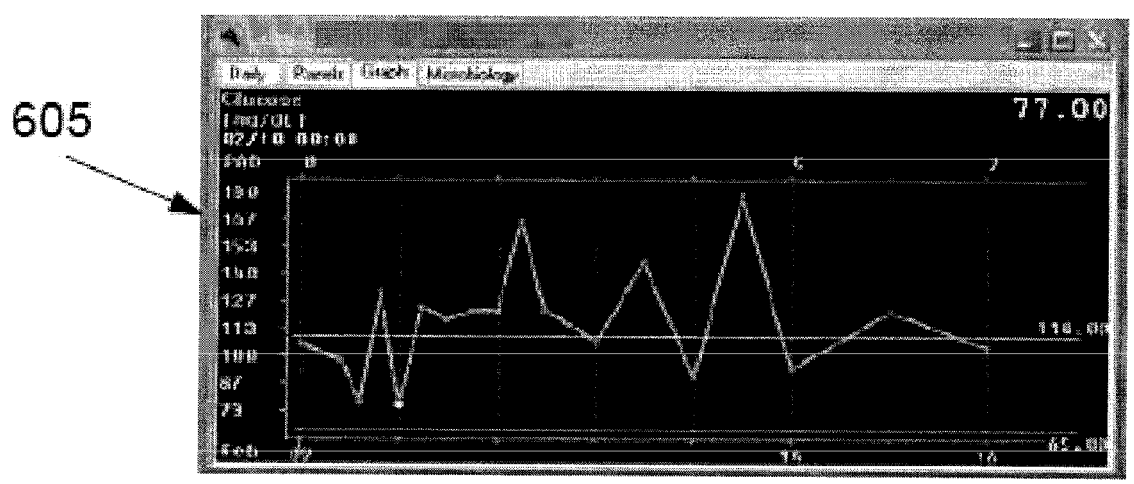
FIG. 6d illustrates a graph of glucose levels in the blood over time.
Figure 6E:
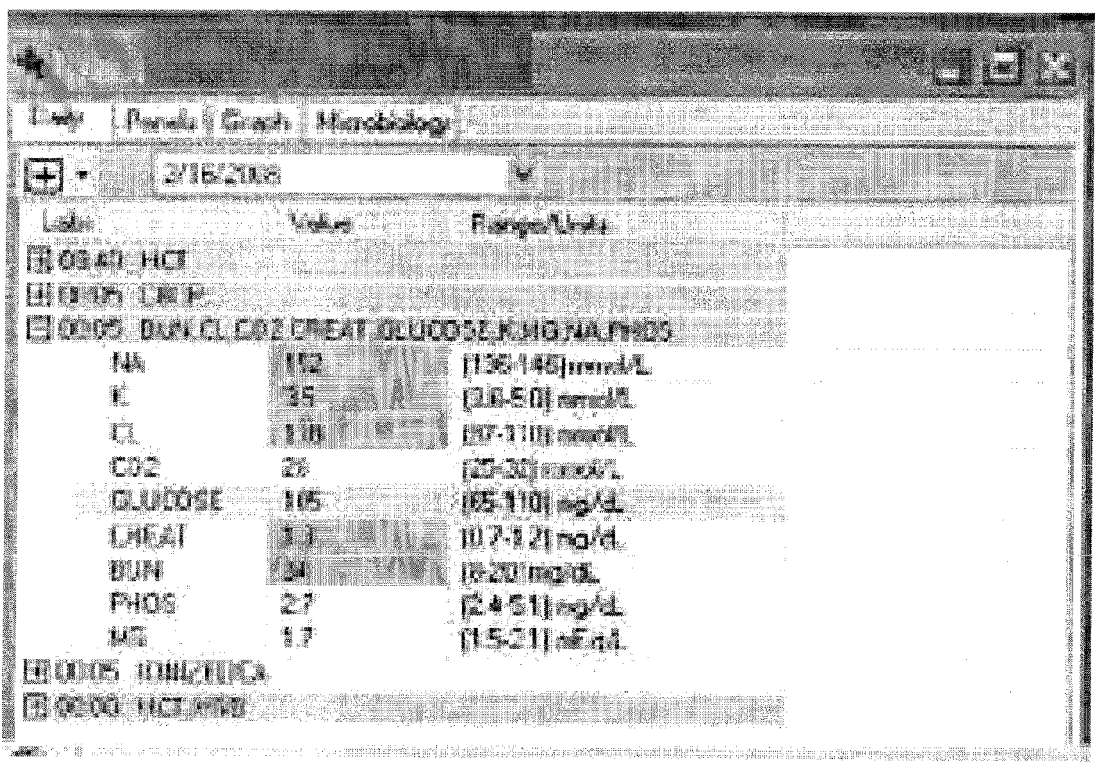
FIG. 6e illustrates a window displaying lab results.

Therefore, when the process determines (at 425) that the current dashboard is linked to another dashboard through the selected item, the process displays (at 430) the other dashboard. FIG. 6 provides one example of another dashboard 600 which is displayed when an item is selected from dashboard 500. Specifically, the user has selected a link in one of the windows or has selected a recommended dashboard from several recommended dashboards. As illustrated, instead of showing several tables and reports, dashboard 600 presents the user with a dashboard that includes a graph of glucose 605 (also shown in exploded format in FIG. 6d), graph of temperature 610 (also shown in exploded format in FIG. 6b), and image view 615 (also shown in exploded format in FIG. 6c) of the patient. In some embodiments, the different dashboards are linked to display situationally appropriate information. For example, a dashboard showing a patient's condition may be linked to another dashboard related to treating that condition.

The process then proceeds to 420, as described above. On the other hand, when the process determines that the current dashboard is not linked to any other dashboard through the selected item, the process (at 435) keeps on displaying the current dashboard. For instance, if an item in dashboard 500 does not link to any other dashboard (e.g., there are no more data related to this item), the current dashboard remains displayed. After 435, the process proceeds to 420 which was described above.

C. Drilling Down to a Dashboard

Some embodiments allow one or more dashboards to be opened up to a predefined configuration. In this way, the user is initially presented with the most relevant information. This concept of initially presenting the most relevant information is also referred to as the drill down concept because it drill through the masses of data and quickly pulls out the data that a user wants to see first. For example, rather than starting with a view containing a list of all radiology scans of a patient, the dashboard may be preconfigured to start with a view of a current chest x-ray and a view of a previous chest x-ray. In some embodiments, the pulling of the data occurs not only at the patient level but also at the user level. In other words, the role of the user (e.g.) doctor, nurse) and the location of the user may also be contributing factors in pulling the relevant data. For instance, a nurse in the cardiac intensive care unit will receive a different set of data than a neurosurgeon.

Some embodiments allow the users to create new dashboards based on the existing dashboards. A user can change the view of one or more window panes in a dashboard to create the new dashboard. For instance, a user can change the display of a window pane from a lab report to a graph of a particular item in the lab report. Or the user can change the view of a window pane from displaying a graph to displaying a table for a set of data values. Some embodiments not only allow the view of a window to be changed but also allow one or more windows of the dashboard to be changed.

Figure 7:
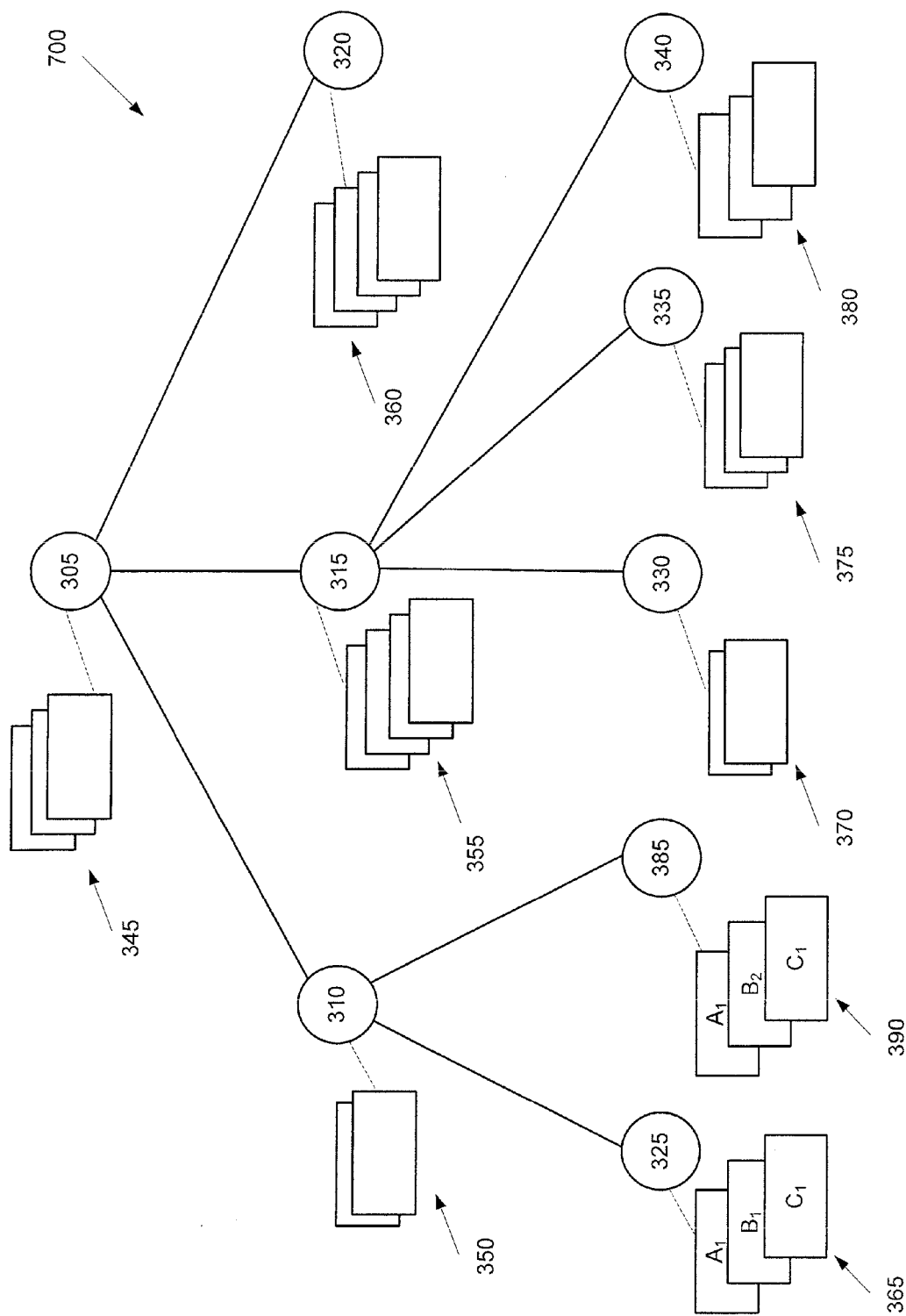
FIG. 7 illustrates a hierarchy of dashboards that provides an example of customizing a view within a window of a dashboard.

FIG. 7 presents a hierarchy 700 of dashboards that illustrate the dashboard customization. The hierarchy has the same dashboards as in FIG. 3 except that a user has created a new dashboard 385 based on an existing dashboard 325. As shown, dashboard 325 has three window panes with three different views $A_1$, $B_1$, and $C_1$. These window panes may, for example, show a CT scan, a lab report, and a graph of oxygen saturation.

In the example of FIG. 7, the user has determined that for a particular patient instead of showing a full lab report in the second window pane, showing a graph of glucose change is more appropriate. The user can create a new dashboard which is similar to dashboard 325 except that the view in the second window pane is changed from the lab report to the graph for glucose change. The new dashboard 385 has three window panes 390. Two of these panes have the same views $A_1$ and $C_1$ as in dashboard 325. The other window pane however, has a new view $B_2$ which shows a graph of glucose change. The new dashboard 385 can be saved. In some embodiments, this new dashboard is saved in the dashboard database or library 120 as illustrated in FIG. 1. From then on, for this particular patient, dashboard 385 (instead of dashboard 325) is opened from dashboard 310. This configuration can also be saved so that the user can also use dashboard 385 for other patients, instead of dashboard 325. For example, when treating a patient with similar medical condition, instead of a default preconfigured dashboard, the user is presented with the reconfigured dashboard 385. In some embodiments, this reconfigured dashboard is provided automatically or as a selectable option (e.g. menu item, tool button).

Figure 8:
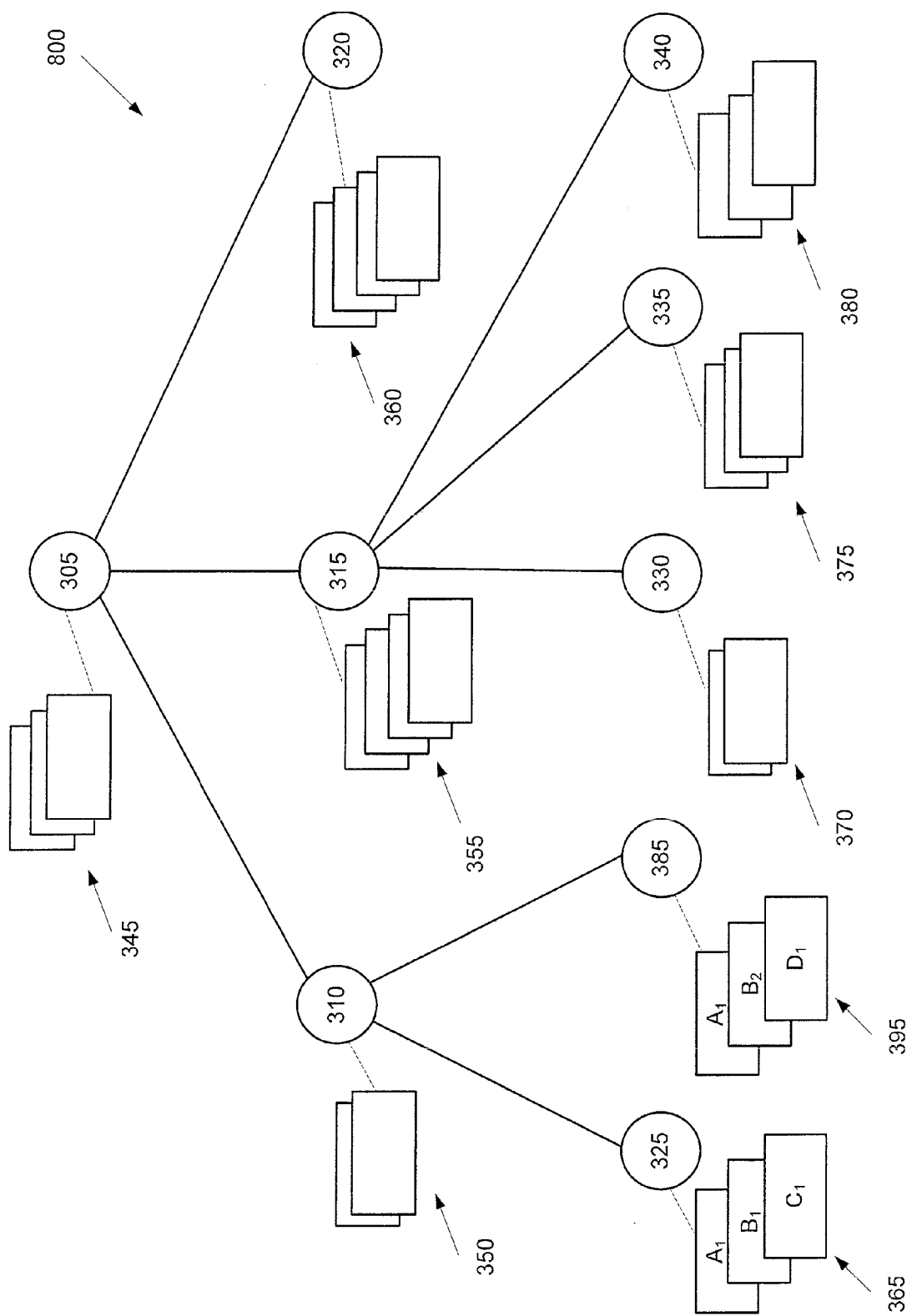
FIG. 8 illustrates a hierarchy of dashboards that provides an example of customizing a window within a dashboard.

FIG. 8 provides another hierarchy 800 of dashboards that illustrate another method of configuring a dashboard. This figure is similar to FIG. 7. However, in this example, the dashboard 385 is customized to include a different combination of panes. This is different from the example shown in FIG. 7 because a window pane has been replaced. Whereas, in the previous example, the window pane has not changed but only its view has changed. Therefore, the new dashboard 385 has three panes 395; two of which are the same as in the previous figure. However, instead of pane $C_1$ a different pane (i.e., pane $D_1$) is included in the dashboard 385. Similar to saving the view configuration, the new pane configuration can also be saved so that the user can use dashboard 385 for other patients.

As described further below, the user has the option of keeping the new dashboard private or allowing the other users to share and/or to modify it. Some embodiments allow the user to link the new dashboard to other dashboards in the hierarchy. For instance, a user might link the new dashboard 385 to dashboard 305. For instance, if dashboard 305 includes a summary list of patients, the user can link the new dashboard 385 to the name of one or more of the patients in dashboard 305 to display dashboard 385 upon selecting those patients in dashboard 305. In other words, the user can drill down to dashboard 385 directly from another dashboard several levels higher in the hierarchy.

Figure 9:
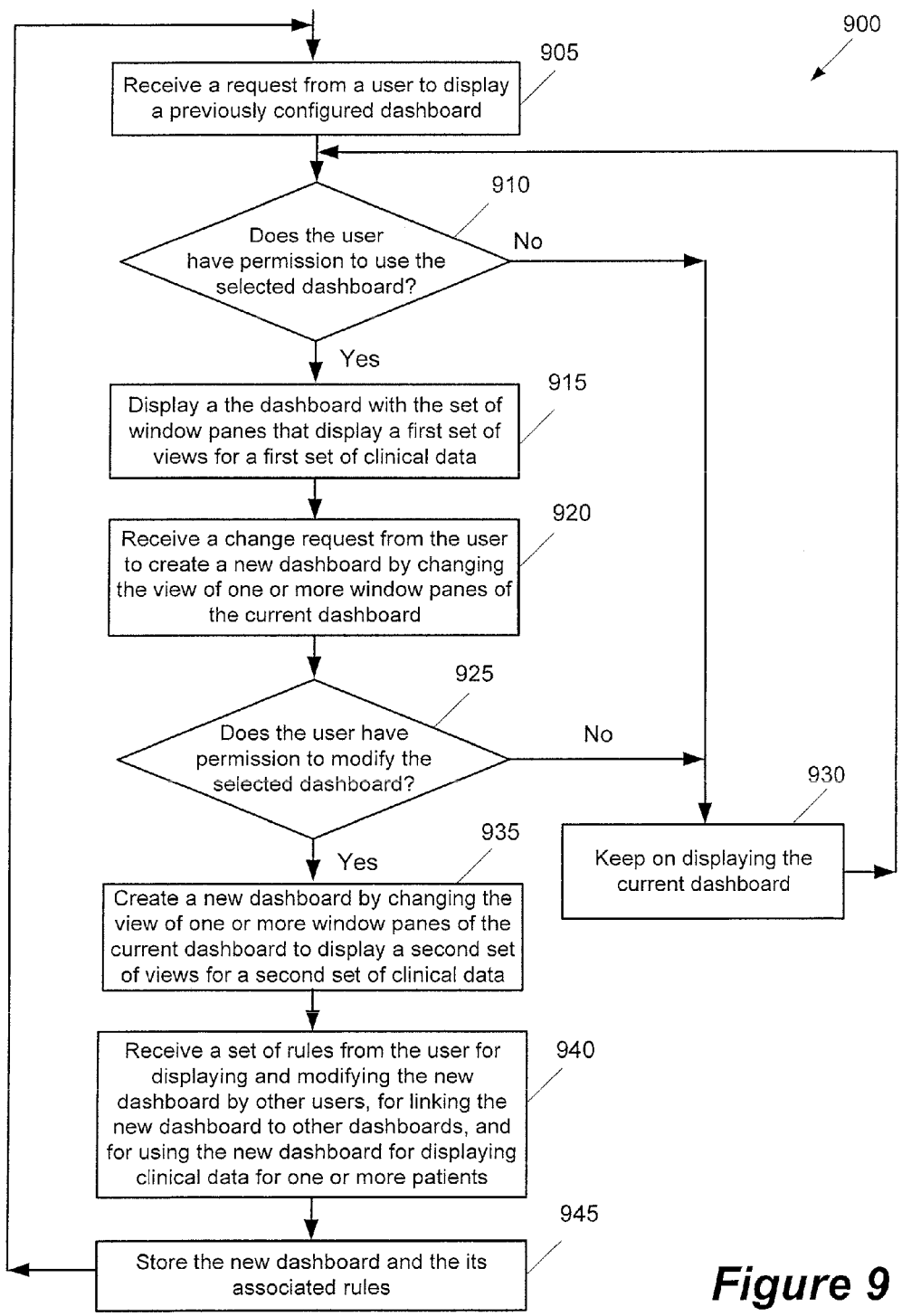
FIG. 9 conceptually illustrates a process for creating a new dashboard based on an existing dashboard by a user.

FIG. 9 conceptually illustrates a process 900 for creating a new dashboard based on an existing dashboard. As shown, the process receives (at 905) a request to display a previously configured dashboard. For instance, the user might have clicked on an item in the patient list window 505 in dashboard 500 that causes dashboard 600 to be displayed.

Figure 10:
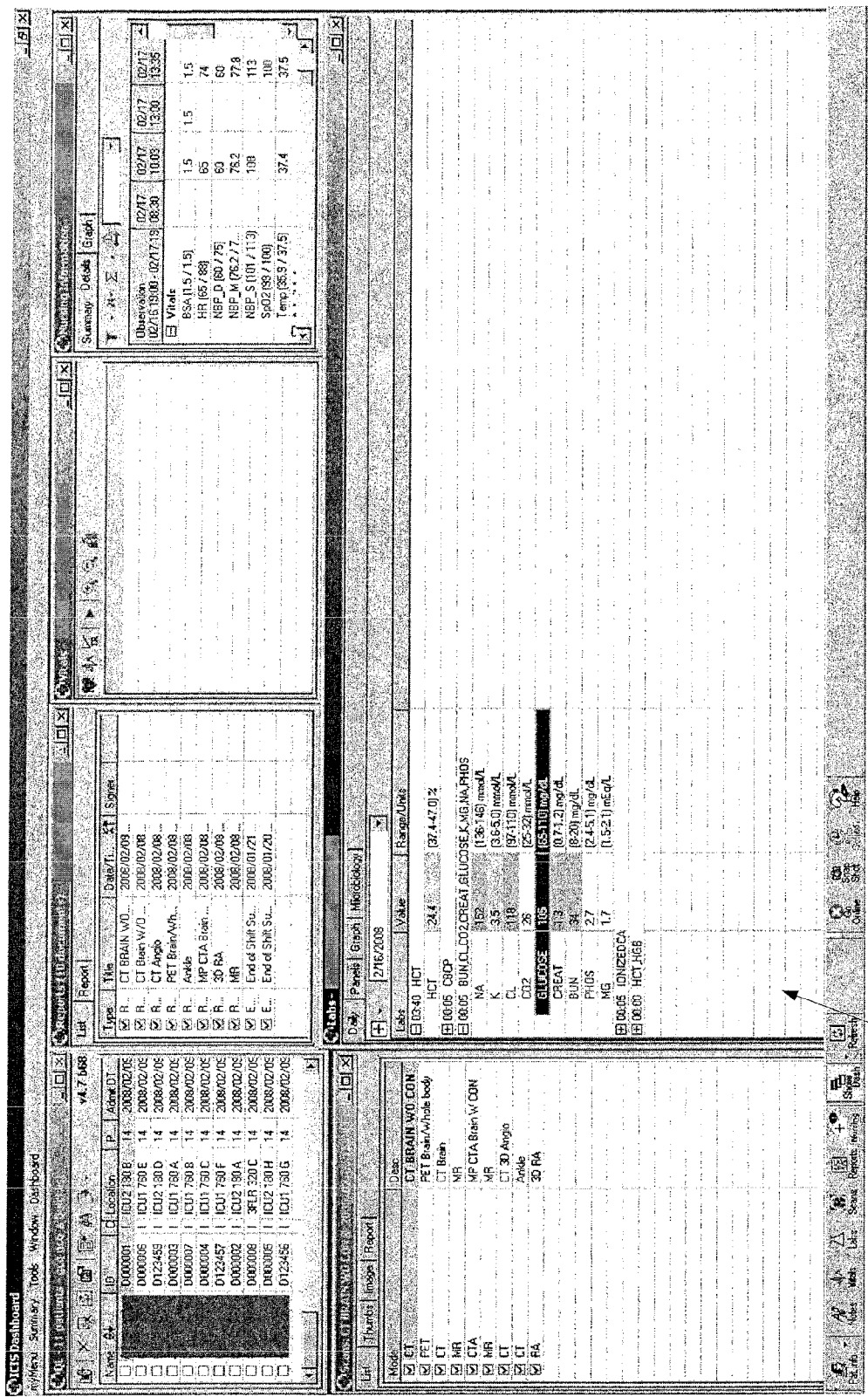
FIGS. 10-11 provides an illustrative example of customizing a view of a window in a dashboard.

Next, at 910, the process determines whether the user has permission to use the selected dashboard. When the user does not have permission to use the selected dashboard, the process (at 930) keeps displaying the current dashboard and proceeds to 910 which was described above. On the other hand, when the user has permission to use the selected dashboard, the process displays (at 915) the selected dashboard. FIG. 10 provides an illustrative example of a dashboard 1000 that is displayed when the user has permission. Specifically, dashboard 1000 contains several windows that include the lab result window 1005.

Next, at 920, the process receives a request to create a new dashboard based on the current dashboard. The user can create this new dashboard by changing the view of one or more window panes of the current dashboard. For instance, the user might decide that instead of the list in the lab result window 1005) displaying a graph for glucose is more appropriate. The process determines (at 925) whether the user has permission to modify the selected dashboard. When the user does not have such permission, the process (at 930) keeps on displaying the current dashboard and proceeds to 910 which was described above.

Figure 11:
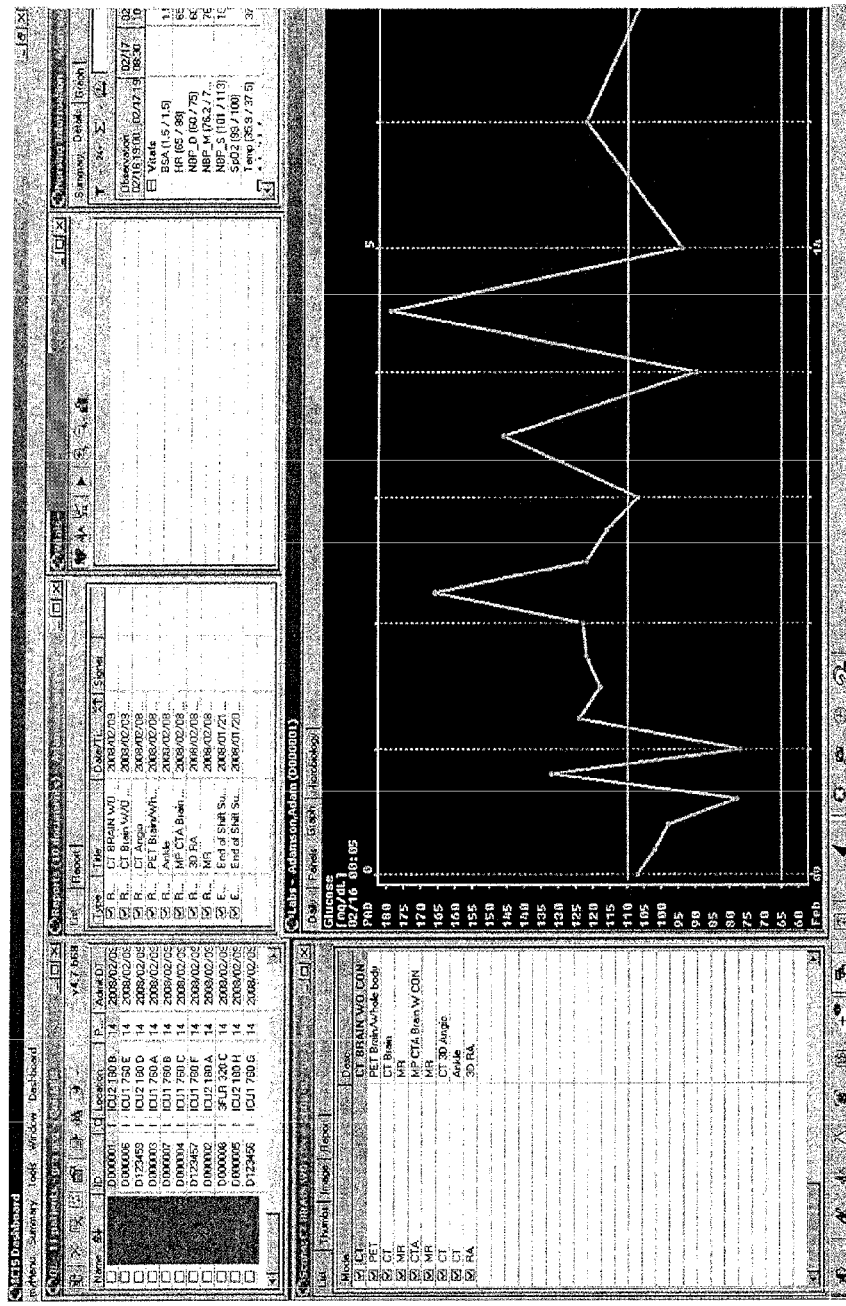
Figure 11A:
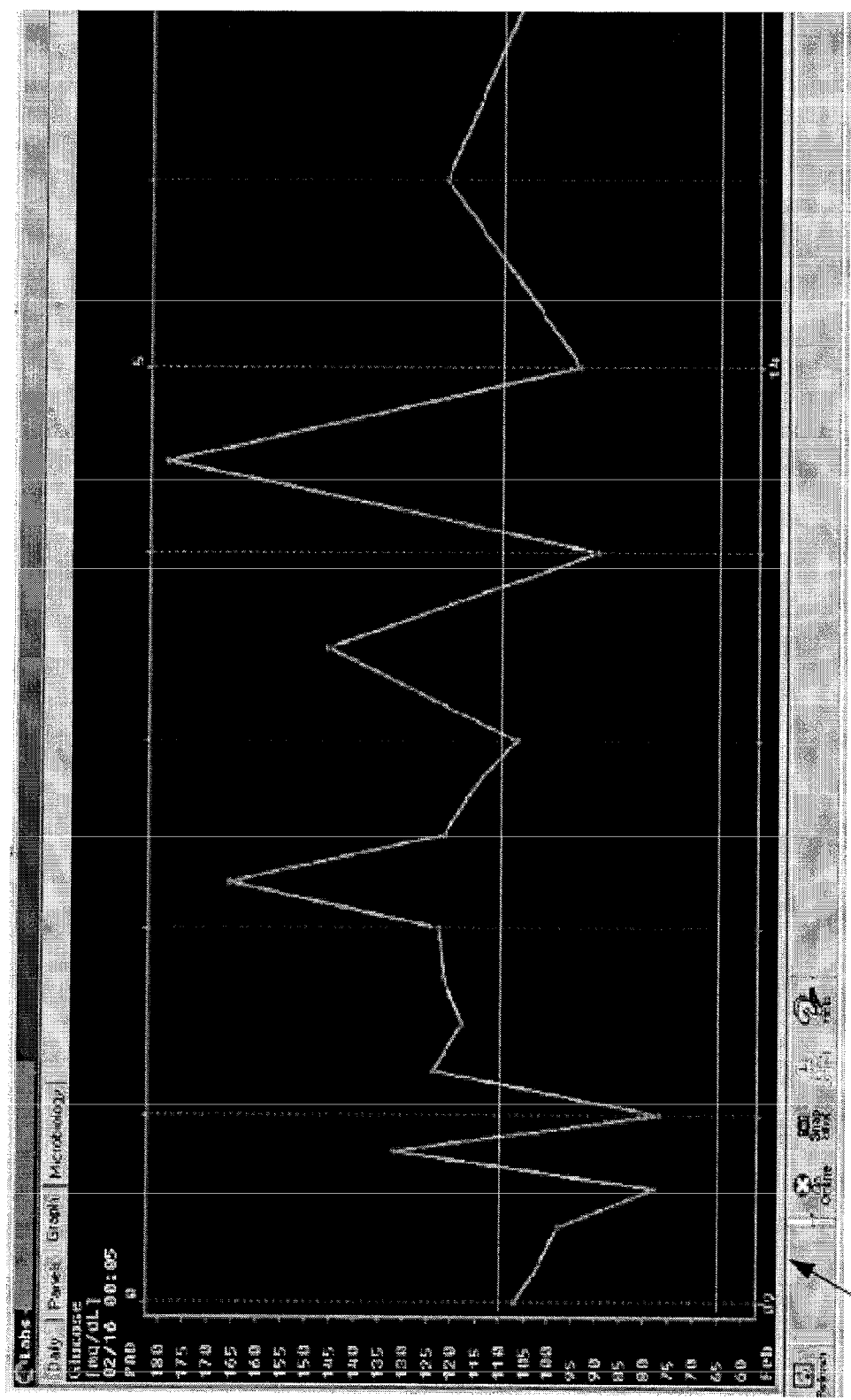
FIG. 11a illustrates a window displaying a graph for glucose levels over time.

On the other hand, when the user has permission to modify the selected dashboard, the process creates (at 935) a new dashboard by making the requested change in the view of one or more window panes. FIG. 11 provides an illustrative example of a new dashboard 1100 which is created based on the existing dashboard 1000. As shown, in the dashboard 1100 the view of the window pane 1005 is changed from showing a list to showing a graph for glucose 1105 (also shown in exploded format in FIG. 11a).

Next, at 940, the user optionally creates a set of rules to determine who can display or modify the new dashboard. The user can also determine for which patient or for which category of patients (e.g., diabetic patients) the new dashboard should be used. The user can also link the new dashboard to one or more other dashboards. For instance, the user can link dashboard 1100 to the name of a particular patient in the summary list to cause the new dashboard to be displayed when the name of that patient is selected by the user.

Some embodiments allow the user to specify whether the new dashboard should be kept private or whether some other users can display the dashboard. Some embodiments also allow the user give permission to some other users to further modify the dashboard. Some embodiments allow the user to link the new dashboard to other dashboards in the hierarchy. Some embodiments allow the user to specify the new dashboard for showing clinical data for one or more patients.

Figure 12:
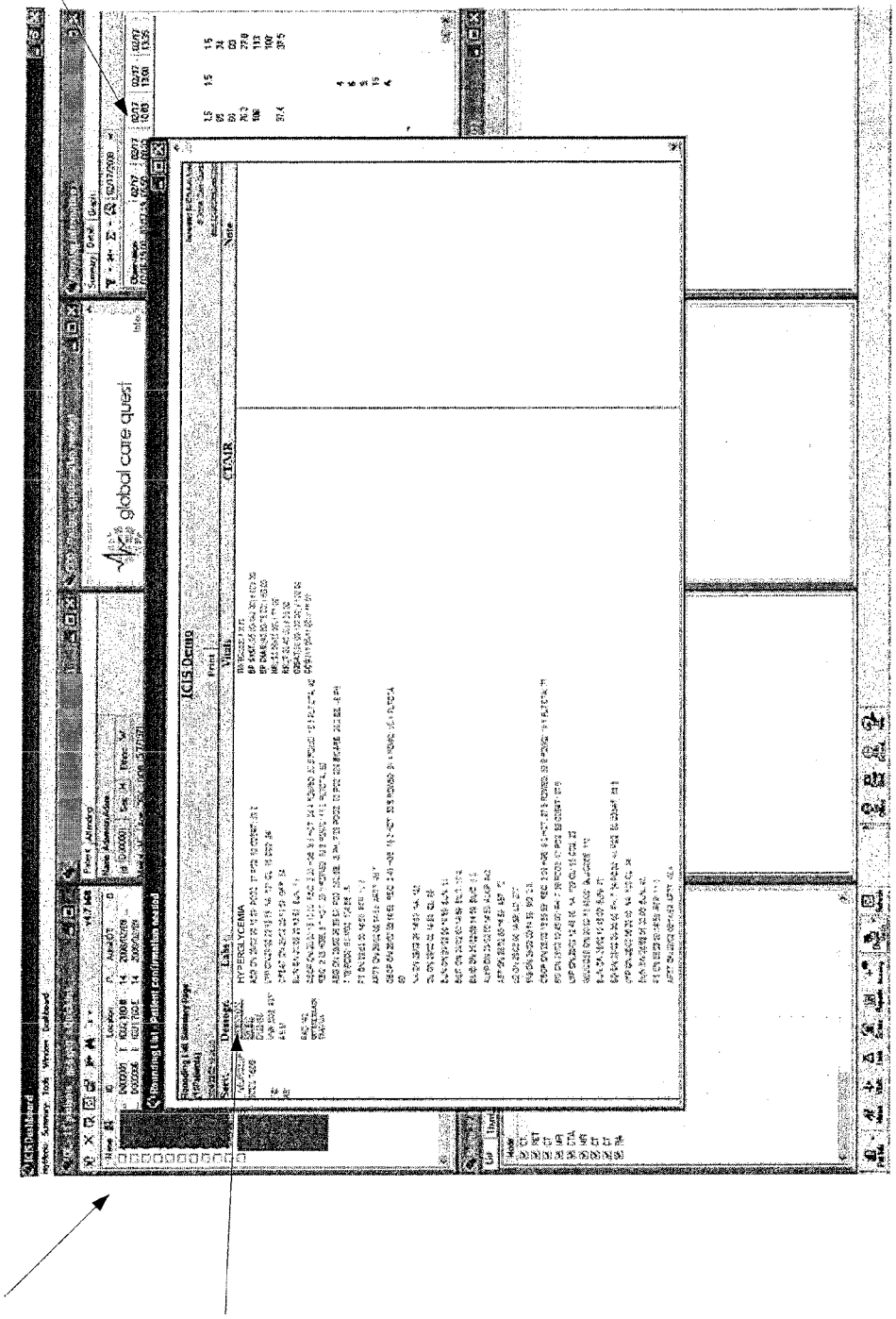
FIGS. 12-13 provides an illustrative example of displaying relevant information when a patient's condition is selected from a patient summary window.
Figure 12A:
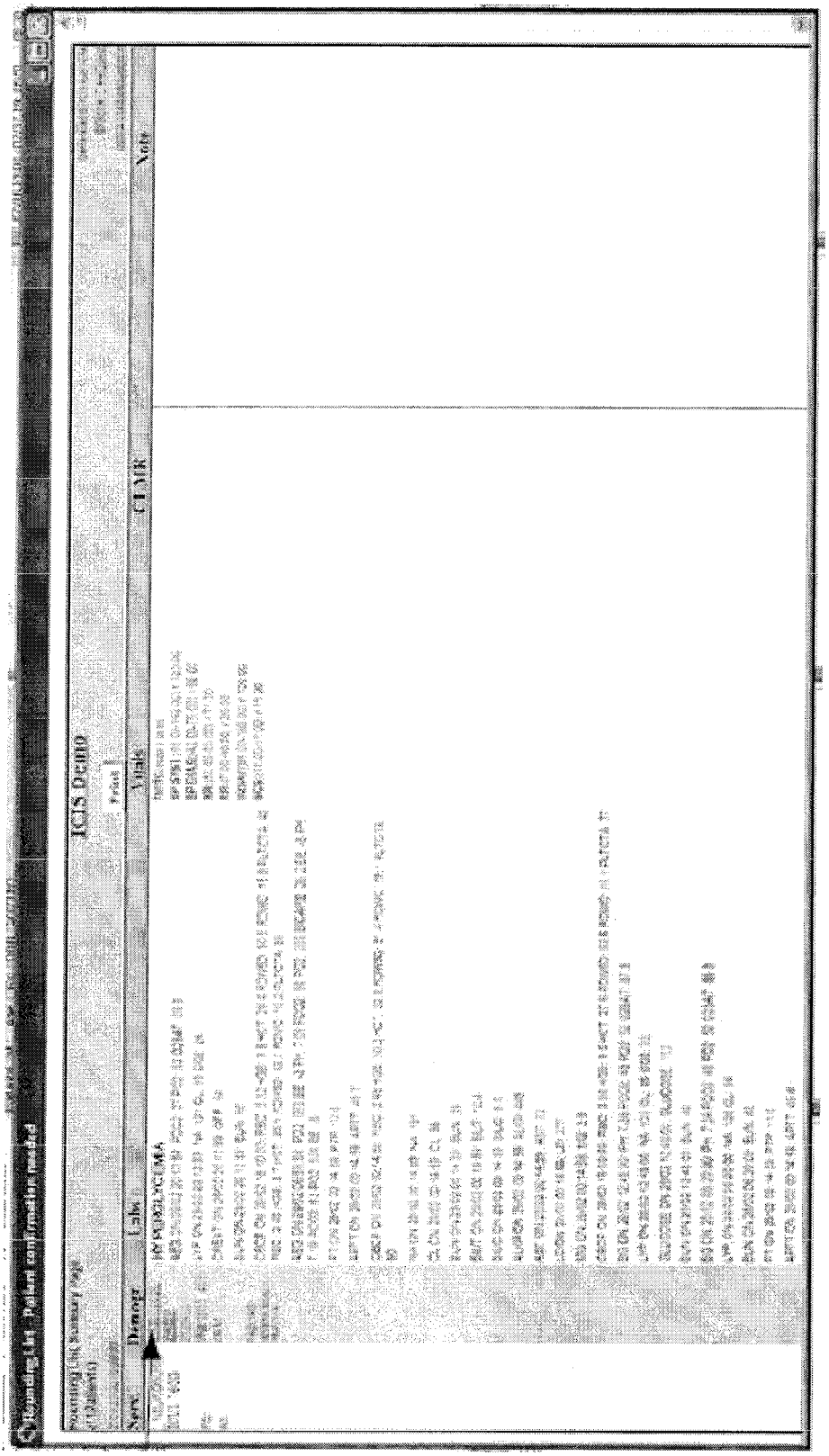
FIG. 12a illustrates a window displaying a summary list.
Figure 13:
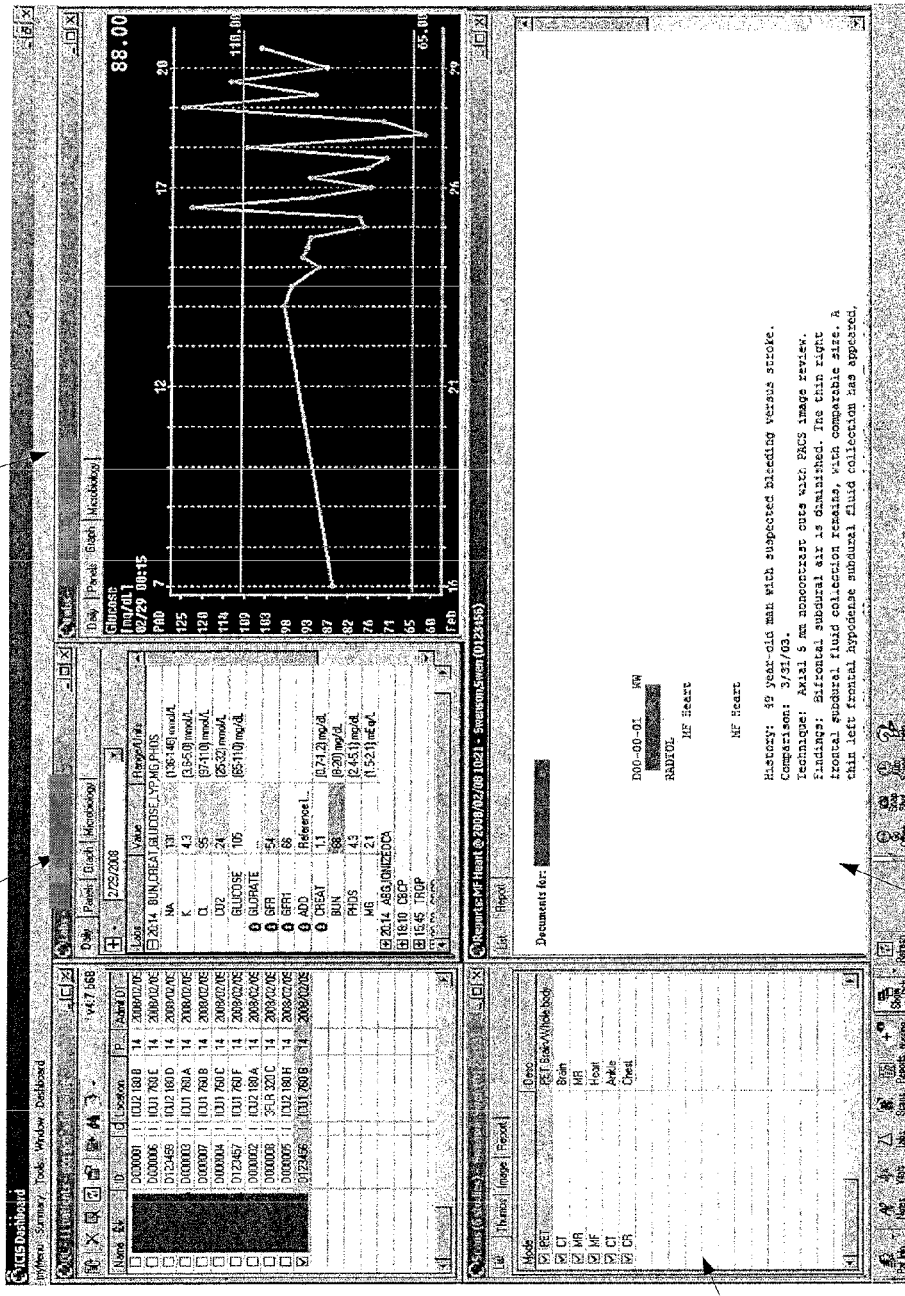

Next, at 945, the process stores the new dashboard and its associated rules for future use. Therefore, when treating a patient with a particular medical condition, the doctor is initially presented with the most relevant information within a dashboard. FIGS. 12-13 provide an illustrative example of displaying a dashboard that drills down to most essential elements. As illustrated in FIG. 12, the user is first presented with a summary list 1205 for one or more patients. In some embodiments, the summary list is presented when a menu item in the menu bar is selected. The summary list 1205 (also shown in exploded format as FIG. 12a) includes a medical condition of the patient 1210. Also, the summary list may include other information such the patient's room number, MR number, PAD, attending name, service name, labs, vital ranges, list of operations (each with date, postoperative diagnosis, operation title, surgeon), impression part of most recent CXR, MRI Scan, CT scan, latest nurse EOSS, 24 hour graphs (e.g., HR, RR, system BP, temperature, oxygen saturation, GCS, MEWS, Apache, SAPS, MAR), etc. In this example, the medical condition states that the patient is being treated for hyperglycemia.

Figure 13A:
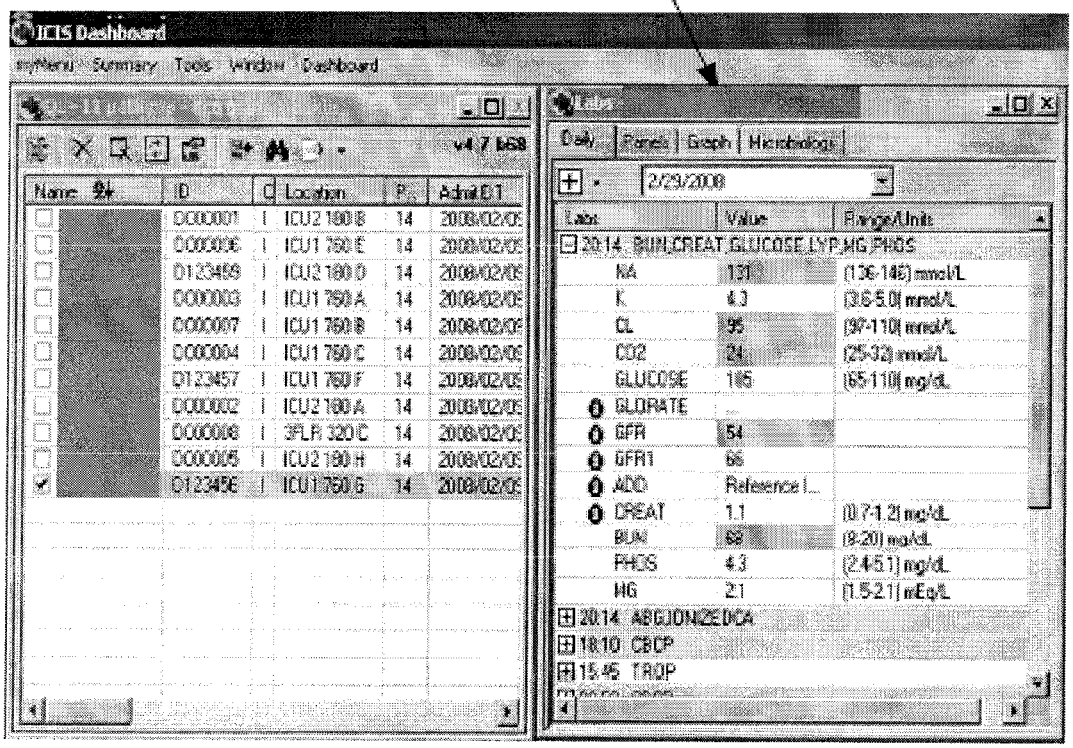
FIG. 13a illustrates a window displaying lab results.
Figure 13B:
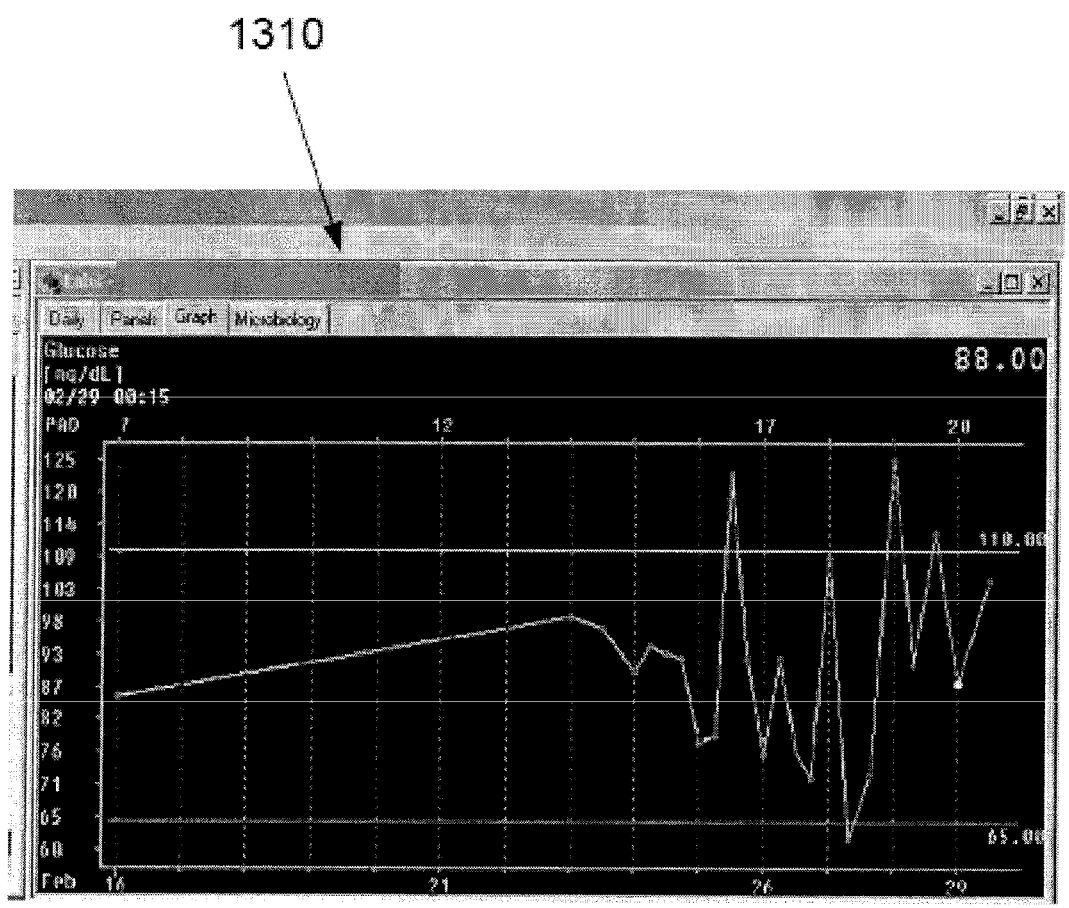
FIG. 13b illustrates a window displaying a glucose graph that provides information about the patient's glucose level.
Figure 13C:
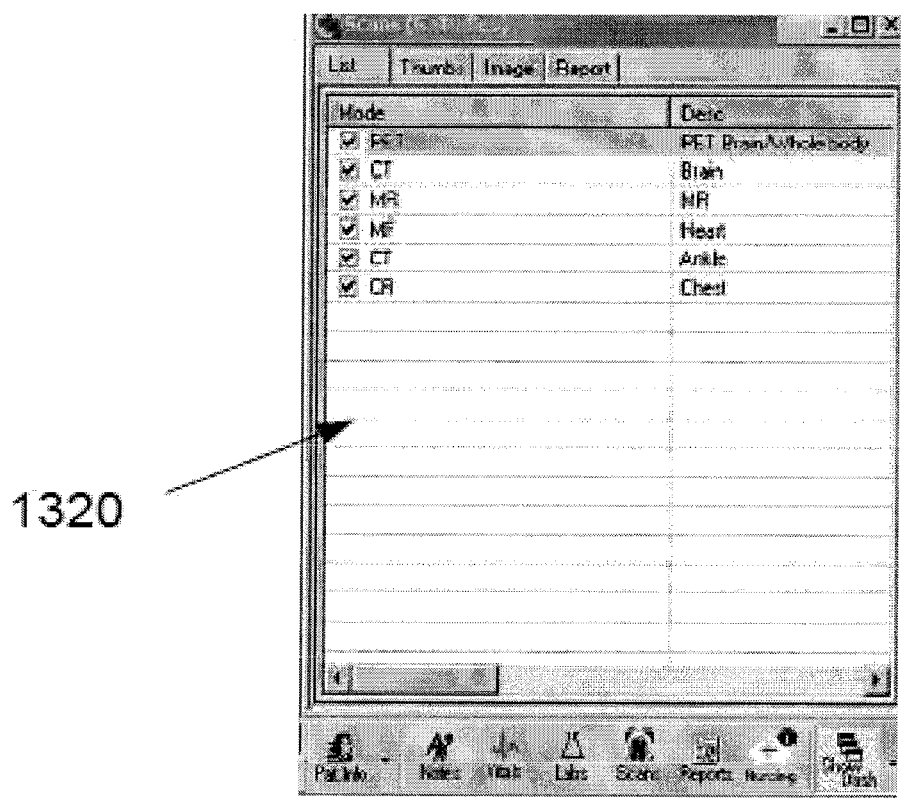
FIG. 13c illustrates a scan window.
Figure 13D:
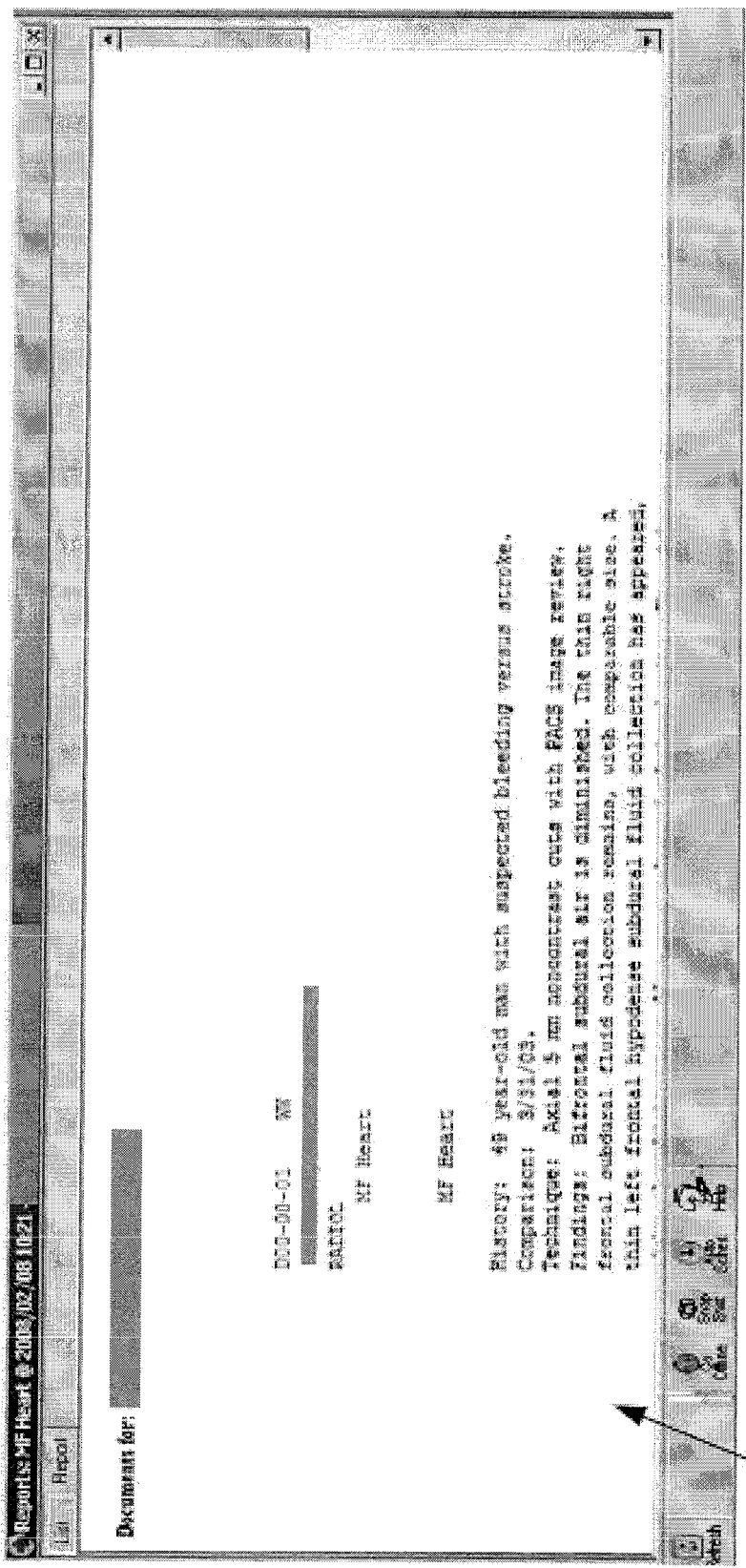
FIG. 13d illustrates a report window report displaying a detailed discussion of the patient's diagnosis.

When the medical condition 1210 is selected (e.g., by clicking on the item)) the user is presented with dashboard 1300 as illustrated in FIG. 13. As illustrated, this dashboard includes (1) a report window 1305 (also shown in exploded format as FIG. 13*d*) that provides a detailed discussion of the patient's diagnosis, (2) glucose graph 1310 (also shown in exploded format as FIG. 13*b*) that provides information about the patient's glucose level, (3) lab results window 1315 (also shown in exploded format as FIG. 13*a*), and (4) scan window 1320 (also shown in exploded format as FIG. 13*c*). Therefore, through a single click of the patient's condition in the summary list 1205, the user is presented with a dashboard that contains relevant information. The goal being that once a condition is identified no additional selections are required to display the information that the user wants to view.

In some embodiments, a selection of a patient name opens up a first dashboard related to the patient's admitting diagnosis and a selection of the medical condition opens up a second dashboard related to treating the medical condition. As discussed above, a dashboard may provide one or more links to other dashboards such as those that describe different protocols for treating a patient with such condition. In some embodiments, when a user selects an item such as the condition in the summary window, the user is presented with several dashboards instead of just one dashboard. For example, a dashboard related to patient's condition and a dashboard related to treating such condition may be presented when a user selects an item.

III. Multi-Phase Informatics Display

Figure 14:
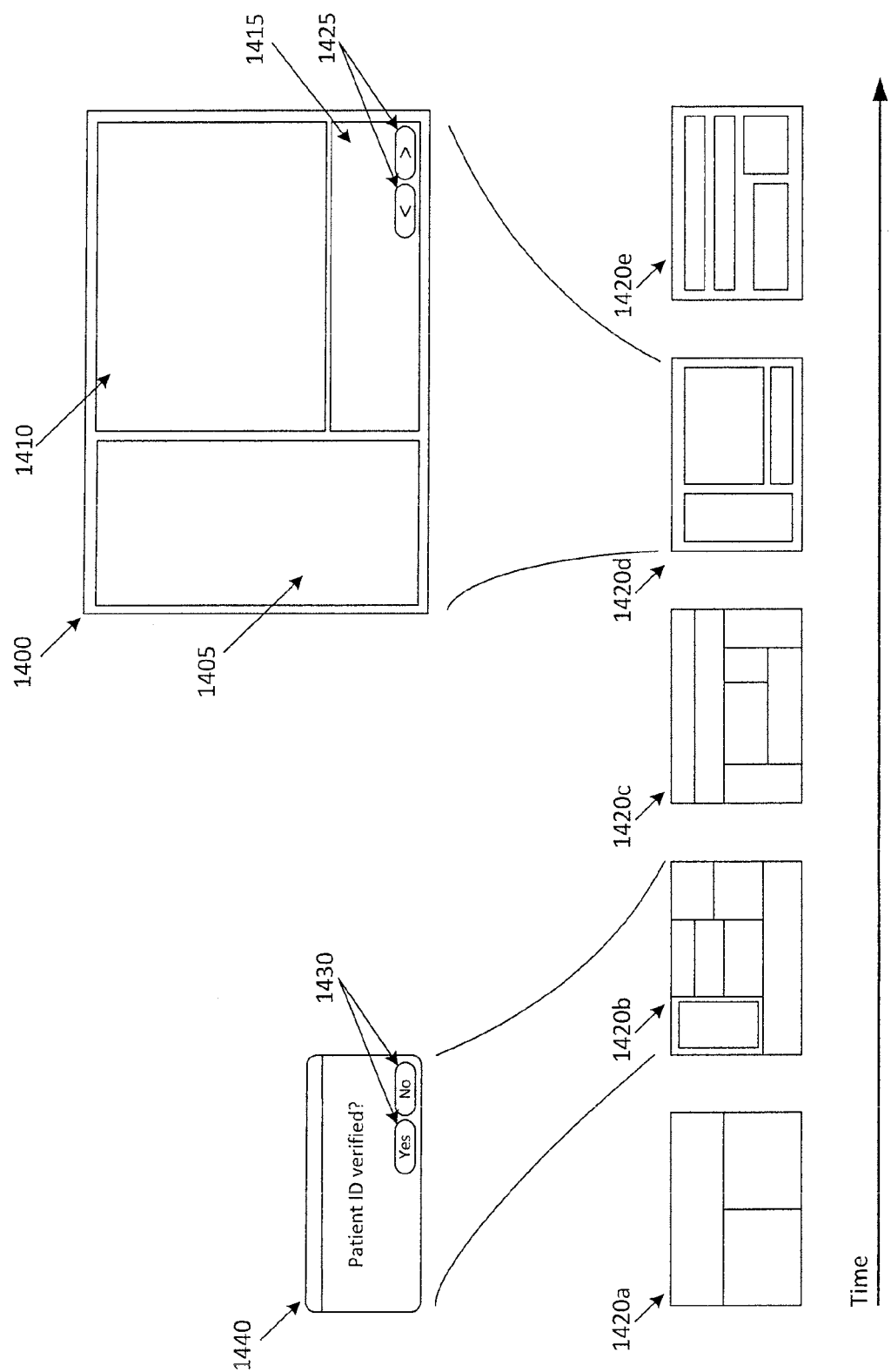
FIG. 14 provides an illustrative example of a set of phase-specific dashboards that can be displayed during a medical procedure.

FIG. 14 illustrates a set of multi-phase informatics dashboards 1420*a-e* of some embodiments. These different dashboards 1420*a-e* may be displayed over the duration of a medical procedure (e.g., a surgical operation). As mentioned above, one or more of these dashboards may be a drill-down dashboard. Each of these dashboards may be pre-configured (by a surgeon who is performing the procedure, or some other user) to display a relevant set of data during a particular stage of the medical procedure (e.g., one dashboard is displayed at a time). For instance, the first dashboard can be a "preference cards" dashboard 1420*a*, the second dashboard a "time out" dashboard 1420*b*, the third dashboard an anesthesiology dashboard 1420*c*, the fourth dashboard a surgery dashboard 1420*d*, and the fifth dashboard a post-operational dashboard 1420*e*.

In the example of FIG. 14, the "preference cards" dashboard 1420*a* is shown first for a particular procedure. This dashboard 1420*a* provides preliminary information necessary to prepare for the procedure (e.g., a list of instruments and supplies necessary to perform the procedure). This information, for example, may be used by nurses who are responsible for gathering the instruments and supplies necessary for the procedure.

The "time out" dashboard 1420*b* is displayed after the "preference cards" dashboard 1420*a*. The "time out" dashboard 1420*b* facilitates a safety check by healthcare professionals (e.g., nurses) before the operation begins. The "time out" dashboard 1420*b* helps the healthcare professionals verify information such as the identity of the patient, the side of the body on which to operate, the body part on which to operate, which procedure is being performed, whether critical drugs are available in case of an emergency, etc. The "time out" dashboard 1420*b* also displays a series of documents, including a consent form, physicians' notes, x-rays, etc. In some embodiments, the "time out" dashboard 1420*b* includes user interface elements (e.g., dialog box 1440, buttons 1430, etc.) that require a user to confirm that certain information (e.g., patient identity, etc.) has been verified.

The anesthesiology dashboard 1420*c* is displayed next. This dashboard 1420*c* may be used, for example, by an anesthesiologist during or after anesthetization of the patient. This dashboard 1420*c* includes information such as blood pressure, heart rate, and other information (e.g., vital signs) that is relevant to a patient's well-being while under anesthesia.

Next, the surgery dashboard 1420*d* is displayed. The exploded view 1400 provides an example layout of a surgery dashboard 1420*d*. The surgery dashboard 1420*d* may include information used by a surgeon, including X-rays, which is displayed in a first pane 1405 of the dashboard. The surgery dashboard 1420*d* also displays patient vital signs (e.g., heart rate, blood pressure, etc.) in a second pane 1415 of the dashboard. Furthermore, the surgery dashboard 1420*d* displays a real-time video feed in a third pane 1410 of the dashboard. This video feed may be captured through a surgeon's tool that is equipped with a camera (e.g., an endoscope, microscope, etc.). The video feed may be used not only by the surgeon to directly assist in performing surgery, but also by other healthcare professionals (e.g., an anesthesiologist who assists in stopping excessive bleeding, a nurse who retrieves medication in case of an emergency, etc.).

Finally, the post-operational dashboard 1420*e* of some embodiments is displayed. This dashboard displays instructions and/or orders to carry out once the procedure has ended. For example, the post-operational dashboard 1420*e* may indicate a set of medication to administer to the patient after the procedure.

As shown by the close-up view 1400, in order to ensure that a particular dashboard is displayed during the relevant stage of the procedure (e.g., the surgery dashboard 1420*d* is displayed during the surgery), some or all of the dashboards have a set of buttons 1425. These buttons 1425 allow a healthcare professional (e.g., nurse, surgeon, anesthesiologist, etc.) to navigate from one dashboard to another. The set of buttons 1425 includes a forward (or "next") button to proceed to the next dashboard. The set of buttons 1425 also includes a back (or "previous") button to proceed to the previous dashboard.

The buttons 1425 may be operated by a cursor control device (e.g., a mouse, touchpad, etc.) that is connected to a computer that runs software that displays the various dashboards. The buttons 1425 may also be operated by a keyboard connected to the computer. Additionally, the dashboards may be displayed on one or more touch screen display devices (e.g., touch screen flat panel LCD monitors) that allow a healthcare professional to operate the set of buttons 1425 by touch.

Navigation from one dashboard to another may also be accomplished by alternate mechanisms in addition to, or in lieu of, visual controls (e.g., the buttons 1425). One such alternate mechanism of some embodiments is voice control. For example, a surgeon speaks a voice command when the anesthesiology dashboard 1420*c* is displayed. This voice command may be a single word, such as "next," or a phrase, such as "next dashboard." The voice command causes the surgery dashboard 1420*d* to be displayed.

Another alternate mechanism of navigating through the various dashboards involves wireless devices (e.g., radio frequency identification, or "RFID" tags). Each healthcare professional, type of healthcare professional (e.g., nurse, surgeon, anesthesiologist, etc.), and/or patient is associated with a particular RFID tag. These RFID tags may be integrated into articles of clothing or accessories (e.g., wristbands, badges, etc.). These RFID tags can be used to indicate the identity of persons (e.g., healthcare professionals, patients) that are present in the room in which the procedure is being performed (e.g., an operating room). For instance, the "preference cards" dashboard 1420*a* is displayed when only nurses are present, the "time out" dashboard 1420*b* is displayed the patient is brought to the room, the anesthesiology dashboard 1420*c* is displayed when the anesthesiologist enters, etc.

In some embodiments, the various dashboards discussed above are displayed on multiple screens. The surgery dashboard 1420*d* may be displayed on a fifty-inch screen, as well as on three twenty one-inch screens in a single operating room. However, some screens may display a dashboard of one stage, while other screens may display a dashboard of a different stage. For example, the abovementioned fifty-inch screen and two of the abovementioned twenty one-inch screens may display the surgery dashboard 1420*c* during surgery. The third twenty one-inch screen may be viewed primarily by the anesthesiologist, and may display the anesthesiology dashboard 1420*c* instead of the surgery dashboard 1420*d*. Additionally, while one or screens display one of the abovementioned stage-specific dashboards, a different screen may display an entirely different dashboard that is not stage-specific (e.g., a "labs" dashboard that shows laboratory results of the patient).

IV. Computer System

Figure 15:
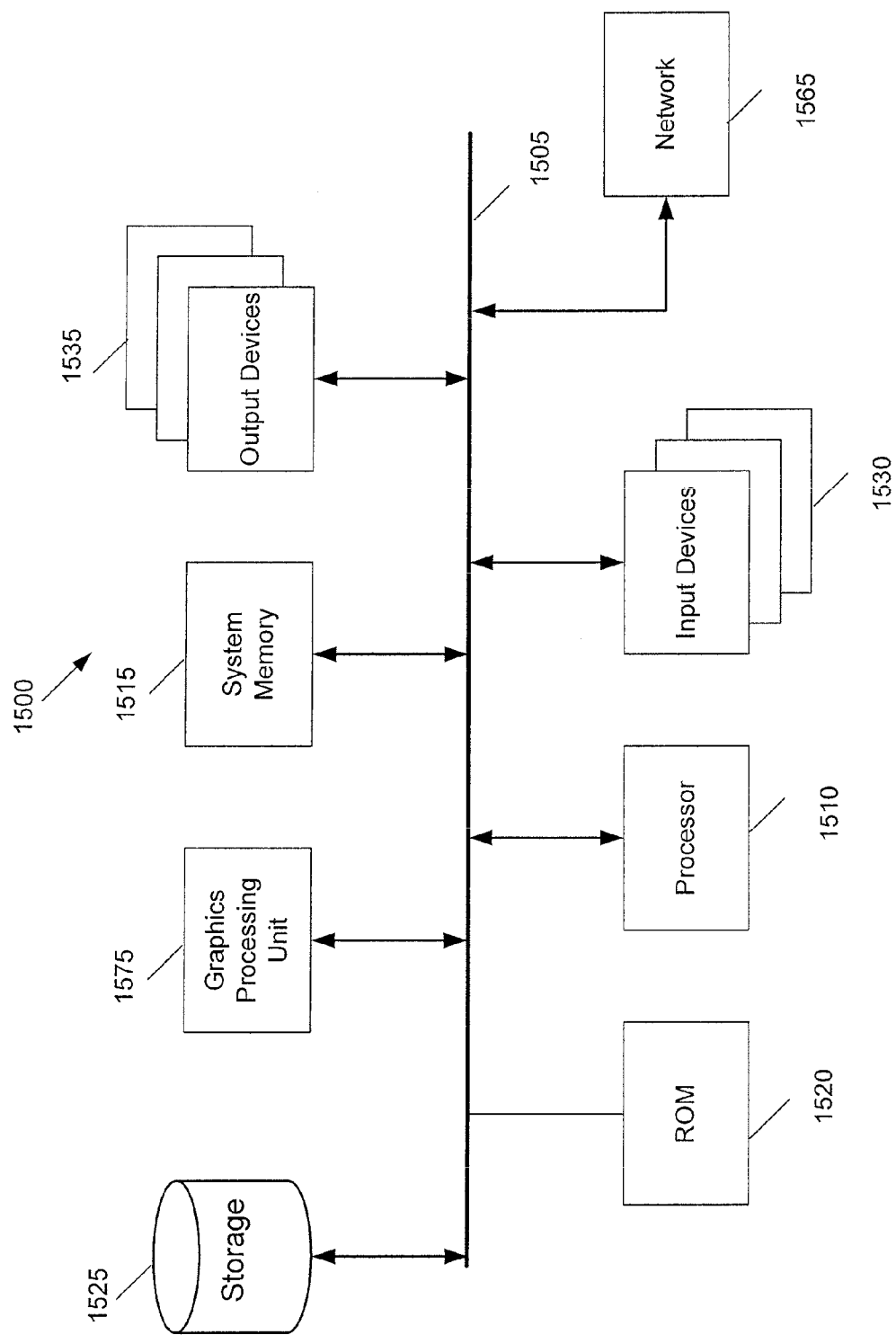
FIG. 15 conceptually illustrates a computer system with which some embodiments of the invention are implemented.

FIG. 15 conceptually illustrates a computer system with which some embodiments of the invention are implemented. The computer system 1500 includes a bus 1505, a processor 1510, a system memory 1515, a read-only memory 1520, a permanent storage device 1525, input devices 1530, and output devices 1535. In some embodiments, the computer system also includes a graphic processing unit (GPU) 1575.

The bus 1505 collectively represents all system, peripheral, and chipset buses that support communication among internal devices of the computer system 1500. For instance, the bus 1505 communicatively connects the processor 1510 with the read-only memory 1520, the system memory 1515, and the permanent storage device 1525.

From these various memory units, the processor 1510 (also referred to as central processing unit or CPU) retrieves instructions to execute and data to process in order to execute the processes of the invention. The read-only-memory (ROM) 1520 stores static data and instructions that are needed by the processor 1510 and other modules of the computer system. The permanent storage device 1525, on the other hand, is a read-and-write memory device. This device is a non-volatile memory unit that stores instruction and data even when the computer system 1500 is off. Some embodiments of the invention use a mass-storage device (such as a magnetic or optical disk and its corresponding disk drive) as the permanent storage device 1525. Other embodiments use a removable storage device (such as a floppy disk or Zip® disk, and its corresponding disk drive) as the permanent storage device.

Like the permanent storage device 1525, the system memory 1515 is a read-and-write memory device. However, unlike storage device 1525, the system memory is a volatile read-and-write memory, such as a random access memory. The system memory stores some of the instructions and data that the processor needs at runtime.

Instructions and/or data needed to perform processes of some embodiments are stored in the system memory 1515, the permanent storage device 1525, the read-only memory 1520, or any combination of the three. For example, the various memory units may contain instructions for processing multimedia items in accordance with some embodiments. From these various memory units, the processor 1510 retrieves instructions to execute and data to process in order to execute the processes of some embodiments.

The bus 1505 also connects to the input and output devices 1530 and 1535. The input devices enable the user to communicate information and select commands to the computer system. The input devices 1530 include alphanumeric keyboards, touch panels, and cursor-controllers. The input devices 1530 also include scanners through which an image can be input to the computer system. The output devices 1535 display images generated by the computer system. For instance, these devices display IC design layouts. The output devices include printers, pen plotters, laser printers, ink-jet plotters, film recorders, and display devices, such as cathode ray tubes (CRT), liquid crystal displays (LCD), or electroluminescent displays.

Also, as shown in FIG. 15, bus 1505 also couples computer 1500 to a network 1565 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 15, the computer system in some embodiments also optionally includes a graphics processing unit (GPU) 1575. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 1510. Also, the computer system 1500 may be used as a personal computer, a workstation, a game console, or the like. Any or all of the components of computer system 1500 may be used in conjunction with the invention. However, one of ordinary skill in the art will appreciate that any other system configuration may also be used in conjunction with the invention.

While the invention has been described with reference to numerous specific details, one of ordinary skill in the art will recognize that the invention can be embodied in other specific forms without departing from the spirit of the invention. In other places, various changes may be made, and equivalents may be substituted for elements described without departing from the true scope of the present invention. For instance, while several example dashboard has been shown as a part of a multi-document interface (MDI), one ordinary skill in the art will recognized that the dashboard can be provided as a group of panes without a parent window. One of ordinary skill in the art will also realize that the dashboards can be displayed on a variety of interface devices in a variety of embodiments, e.g. computer displays, PDAs, cell phones, etc. Further, one of ordinary skill in the art will recognize that several of the views of different windows may be combined to provide a unified view. For instance, instead of selecting a tab to view graphs of lab results, a window may include both the lab results and one or more graphs.

What is claimed is:

1. A system for displaying clinical information on a computer or a computer network, the system comprising:
   a computer or a computer network;
   an interface having a first display area and a second display area, the first display area and the second display area being monitors; and
   two or more dashboards, the two or more dashboards each having one or more window panes, the two or more dashboards corresponding to a multi-stage medical operation, each dashboard corresponding to a stage in the multi-stage medical operation, the two or more dashboards being preconfigured to display a set of data during a particular stage of the medical operation based upon both a patient and a user performing the multi-stage medical operation,
   wherein a first dashboard is displayed in the first display area, and the remaining dashboards are displayed as selectable icons in the second display area, the first dashboard and the remaining dashboards being linked through the selectable icons, the first dashboard being displayed in the first display area based upon detection of a wireless device in the operating room,
   wherein the first dashboard and the remaining dashboards can be switched by an element, wherein the element switches the first dashboard displayed in the first display area with a dashboard corresponding to a selectable icon displayed in the second display area, and
   wherein a person pre-configures each of the two or more dashboards to customize the two or more dashboards, so that the data displayed in the first display area corresponds to the particular stage of the medical operation.

2. The system of claim 1, wherein the second display area is either above the first display area, to the side of the first display area, or partially overlapping the first display area.

3. The system of claim 1, wherein said element is selected from a group consisting of a touch sensitive element, scrolling element, cursor, switch, automated element, tag, RFID tag, voice control, or wireless device.

4. The system of claim 1, wherein said two or more dashboards includes five separate dashboards for a five stage operation.

5. The system of claim 4, wherein said separate stages are 1) a preference-card stage, 2) a time-out stage, 3) an anesthetic stage, 4) an operation stage, and 5) a post-operation stage.

6. The system of claim 1, wherein the device allows for automatic scrolling of the two or more dashboards.

7. The system of claim 1, further comprising linking said system to input and output devices.

8. The system of claim 1, wherein the wireless device is an RFID tag.

9. The system of claim 8, wherein the RFID tag is integrated into an article of clothing.

10. The system of claim 8, wherein the RFID tag is associated with a first set of dashboards, and a second RFID tag is associated with a second set of dashboards.

11. The system of claim 10, wherein the RFID tag is a nurse RFID tag that is associated with the first set of dashboards.

12. The system of claim 11, wherein the RFID tag is a doctor RFID tag that is associated with the second set of dashboards.

13. The system of claim 1, wherein the multi-stage medical operation is a multi-stage surgical operation.

14. A method for launching clinical information on a computer interface in an operating room, the method comprising the steps of:
   providing a computer interface;
   providing two or more dashboards, the two or more dashboards corresponding to a multi-stage medical operation, each dashboard corresponding to a stage in the multi-stage medical operation, the two or more dashboards being preconfigured to display a set of data during a particular stage of the medical operation based upon both a patient and a user performing the multi-stage medical operation;
   detecting a wireless device in the operating room;
   displaying a first dashboard in a first display area of the interface based upon the detection of the wireless device in the operating room, the first display area being a monitor;
   displaying the remaining dashboards as selectable icons in a second display area of the interface, the second display area being a second monitor;
   selecting a selectable icon from the second display area, and displaying the dashboard corresponding to the selected selectable icon in the first display area; and
   displaying the first dashboard as a selectable icon in the second display area, the two or more dashboards being linked through the selectable icons, and
   wherein a person pre-configures each of the two or more dashboards to customize the two or more dashboards, so that the data displayed in the first display area corresponds to the particular stage of the medical operation.

15. The method of claim 14, further comprising selecting additional selectable icons to display additional dashboards in the first display area for a multi-stage procedure or operation, wherein the additional selectable icons selected are displayed in the first display area.

16. The method of claim 14, wherein the selecting step further comprises an element that allows for a selectable icon from the second display area to be picked.

17. The method of claim 16, wherein the element is selected from a group consisting of a touch sensitive element, scrolling element, cursor, switch, automated element, tag, RFID tag, voice control, or wireless device.

18. The method of claim 16, wherein the element allows for automated scrolling of the dashboards.

19. The method of claim 16, wherein the element is worn or carried by a user.

20. The method of claim 14, wherein the step of displaying the remaining dashboards as selectable icons in a second display area additionally comprises displaying the first dashboard as a selectable icon in the second display area.

21. The method of claim 14, wherein the first dashboard has a predefined configuration based upon a selected user profile.

22. The method of claim 14, wherein the two or more dashboards have multiple window panes.

23. The method of claim 14, wherein the wireless device is an RFID tag.

24. The method of claim 14, further comprising determining if the user has permission to modify the dashboards.

25. A method for launching clinical information on a computer interface in an operating room, the method comprising the steps of:
   providing a computer interface, and two or more dashboards, the two or more dashboards each having one or more window panes, the two or more dashboards corresponding to a multi-stage medical operation, each dashboard corresponding to a stage in the multi-stage medical operation, the two or more dashboards being preconfigured to display a set of data during a particular stage of the medical operation based upon both a patient and a user performing the multi-stage medical operation;

detecting a wireless device in an operating room;

displaying a first dashboard in a first display area of the interface based upon the detection of the wireless device in the operating room, the first display area being a monitor;

displaying the remaining dashboards as selectable icons in a second display area of the interface, the second display area being a second monitor; and selecting an item in a window pane of the first dashboard and displaying the corresponding dashboard configured to the item selected in the first display area of the interface, the two or more dashboards being linked through the selectable icons, and wherein a person pre-configures each of the two or more dashboards to customize the two or more dashboards, so that the data displayed in the first display area corresponds to the particular stage of the medical operation.

26. The method of claim 25, further comprising hiding or closing the first dashboard in the first display area and displaying the corresponding dashboard configured to the item selected in the first display area.

27. The method of claim 25, wherein the corresponding dashboard configured to the item selected is displayed in a third display area that partially overlaps the first display area.

28. The method of claim 25, wherein the item selected may correspond to a selectable icon and dashboard displayed in the second display area.

29. The method of claim 25, wherein the wireless device is an RFID tag.

* * * * *